United States Patent [19]

Matsuo et al.

[11] Patent Number: 4,866,091

[45] Date of Patent: Sep. 12, 1989

[54] ALKANESULFONANILIDE DERIVATIVES, PROCESSES FOR PREPARATION THEREOF AND PHARMACEUTICAL COMPOSITION COMPRISING THE SAME

[75] Inventors: Masaaki Matsuo, Toyonaka; Kiyoshi Tsuji, Kishiwada; Nobukiyo Konishi, Nagaokakyo, all of Japan

[73] Assignee: Fujisawa Pharmaceutical Co., Ltd., Osaka, Japan

[21] Appl. No.: 202,017

[22] Filed: Jun. 2, 1988

Related U.S. Application Data

[63] Continuation-in-part of Ser. No. 132,334, Dec. 14, 1987.

[30] Foreign Application Priority Data

Dec. 31, 1986 [GB] United Kingdom ............... 8631083
May 29, 1987 [GB] United Kingdom ............... 8712647
Oct. 23, 1987 [GB] United Kingdom ............... 8724903

[51] Int. Cl.[4] .................. C07C 161/00; C07C 143/74; C07D 307/02
[52] U.S. Cl. .................. 514/471; 514/522; 514/524; 514/525; 514/538; 514/600; 514/605; 558/413; 564/79; 564/99; 560/156; 549/475; 549/480
[58] Field of Search ............ 558/413; 564/99, 79; 514/524, 600, 605, 471, 522, 525, 538; 560/156; 549/475, 480

[56] References Cited

U.S. PATENT DOCUMENTS

| | | | |
|---|---|---|---|
| 3,531,522 | 10/1970 | Nelson et al. | 564/99 |
| 3,531,523 | 10/1970 | Nelson et al. | 564/79 |
| 3,840,597 | 10/1974 | Moore et al. | 564/99 |
| 3,906,024 | 9/1975 | Moore et al. | 558/413 |
| 4,465,508 | 8/1984 | Barton et al. | 564/99 |
| 4,523,034 | 6/1985 | Porg et al. | 564/79 |

OTHER PUBLICATIONS

Journal of Medicinal Chemistry, 1975, vol. 18, No. 4, pp. 386 to 391.

*Primary Examiner*—Paul Lieberman
*Assistant Examiner*—Helene Kirschner
*Attorney, Agent, or Firm*—Oblon, Spivak, McClelland, Maier & Neustadt

[57] ABSTRACT

This invention relates to new alkane-sulfonanilide derivatives of the formula:

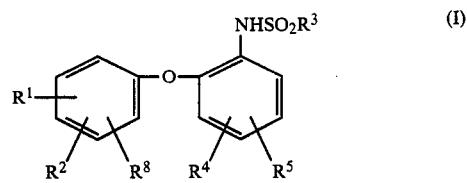

wherein
$R^1$, $R^2$ and $R^8$ are each hydrogen, cyano, halogen, lower alkyl, halo (lower) alkyl, lower alkylthio, lower alkylsulfinyl, lower alkylsulfonyl or lower alkoxy,
$R^3$ is lower alkyl,
$R^4$ is acyl, cyano, carboxy, hydroxy(lower)-alkyl, mercapto, lower alkylthio, lower alkylsulfinyl, lower alkylsulfonyl, 5-membered unsaturated heterocyclic group which may have amino, lower alkanoylamino, lower alkylthio or lower alkylsulfonyl, phenylthio which may have nitro or amino, lower alkanoyl(lower)alkenyl or a group of the formula:

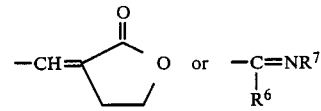

wherein
$R^6$ is hydrogen, amino or lower alkyl and
$R^7$ is hydroxy, lower alkoxy, carboxy(lower)alkoxy, lower alkoxycarbonyl(lower)alkoxy, ureido or thioureido, and
$R^5$ is hydrogen, halogen, lower alkyl or lower alkanoyl, and pharmaceutically acceptable salts thereof.

More particularly, it relates to alkanesulfonanilide derivatives and pharmaceutically acceptable salts thereof which have antiinflammatory activities and analgesic activities, to processes for the preparation thereof, to a pharmaceutical composition comprising the same and to a method for the treatment of inflammatory disease or pains in human being and animals.

18 Claims, No Drawings

ALKANESULFONANILIDE DERIVATIVES, PROCESSES FOR PREPARATION THEREOF AND PHARMACEUTICAL COMPOSITION COMPRISING THE SAME

This is a continuation-in-part of Ser. No. 132,334 filed Dec. 14, 1987.

This invention relates to new alkanesulfonanilide derivatives and pharmaceutically acceptable salts thereof. More particularly, it relates to alkanesulfonanilide derivatives and pharmaceutically acceptable salts thereof which have antiinflammatory activities and analgesic activities, to processes for the preparation thereof, to a pharmaceutical composition comprising the same and to a method for the treatment of inflammatory disease or pains in human being and animals.

The objective alkanesulfonanilide derivatives and pharmaceutically acceptable salts thereof are novel and can be represented by the following general formula (I):

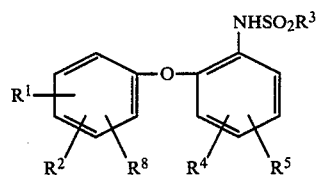

(I)

wherein
$R^1$, $R^2$ and $R^8$ are each hydrogen, cyano, halogen, lower alkyl, halo(lower)alkyl, lower alkylthio, lower alkylsulfinyl, lower alkylsulfonyl or lower alkoxy,
$R^3$ is lower alkyl, or mono or di-lower alkylamino,
$R^4$ is acyl, cyano, carboxy, hydroxy(lower)alkyl, mercapto, lower alkylthio, lower alkylsulfinyl, lower alkylsulfonyl, 5-membered unsaturated heterocyclic group which may have amino, lower alkanoylmino, lower alkylthio or lower alkylsulfonyl, phenylthio which may have nitro or amino, lower alkanoyl(lower)alkenyl or a group of the formula:

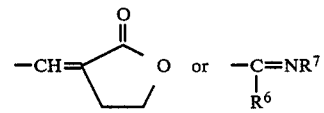

wherein
$R^6$ is hydrogen, amino or lower alkyl and
$R^7$ is hydroxy, lower alkoxy, carboxy(lower)alkoxy, lower alkoxycarbonyl(lower)alkoxy, ureido or thioureido, and
$R^5$ is hydrogen, halogen, lower alkyl or lower alkanoyl, and pharmaceutically acceptable salts thereof.

According to this invention, the new alkanesulfonanilide derivatives (I) and salts thereof can be prepared by various processes which are illustrated by the following reaction schemes:

Process 1

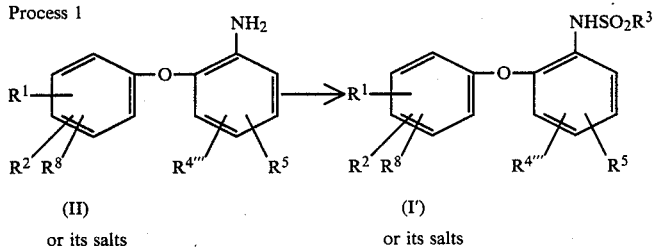

(II)
or its salts (I')
or its salts

Process 2

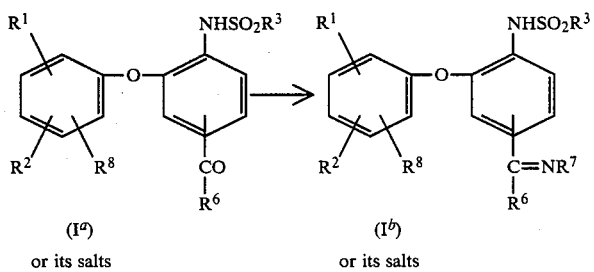

($I^a$)
or its salts ($I^b$)
or its salts

Process 3

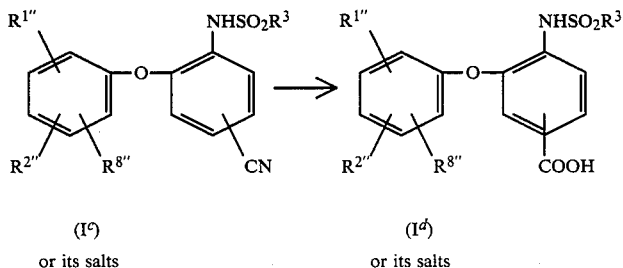

($I^c$)
or its salts ($I^d$)
or its salts

-continued
Process 4
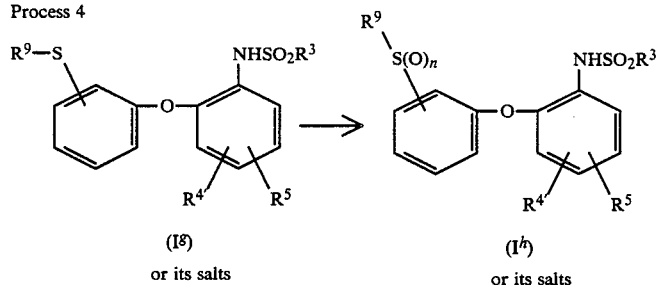
(I$^g$)
or its salts
(I$^h$)
or its salts
Process 5
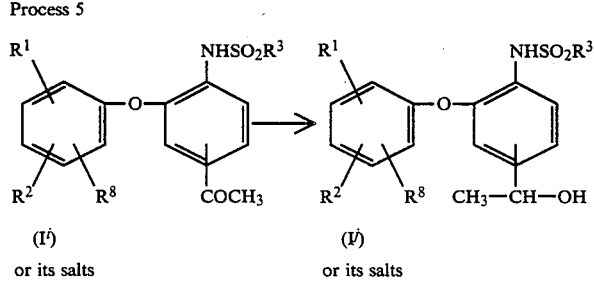
(I$^i$)
or its salts
(I$^j$)
or its salts
Process 6
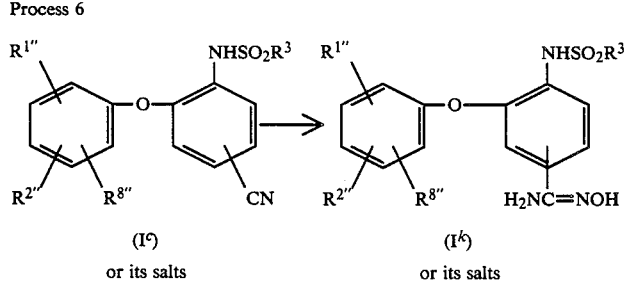
(I$^c$)
or its salts
(I$^k$)
or its salts
Process 7
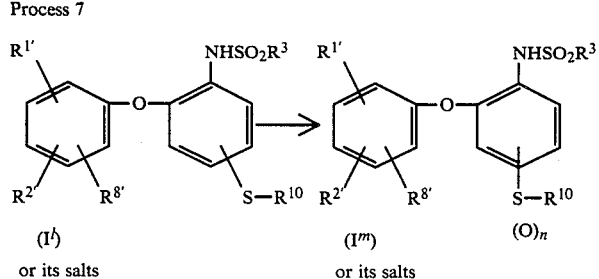
(I$^l$)
or its salts
(I$^m$)
or its salts
Process 8
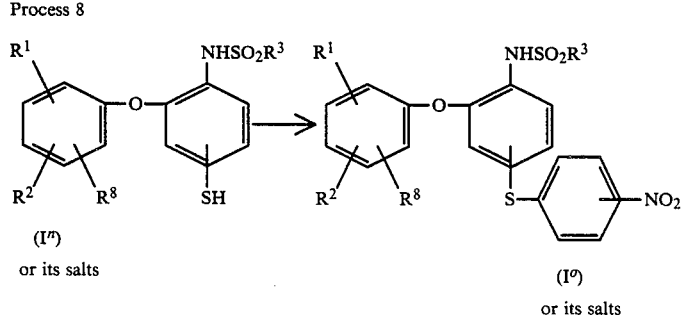
(I$^n$)
or its salts
(I$^o$)
or its salts -continued
Process 9
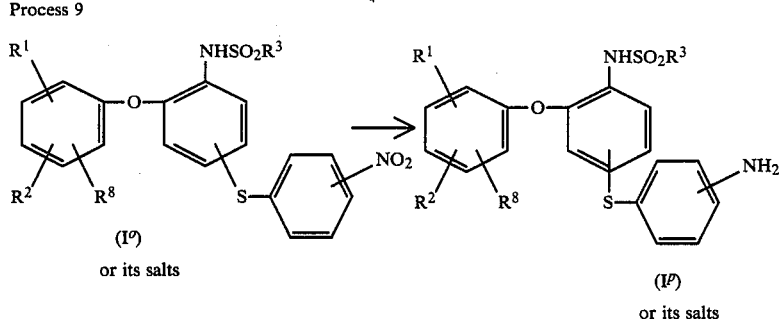
(I°) or its salts
(I^p) or its salts
Process 10
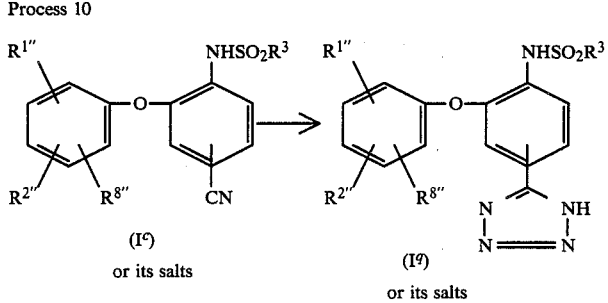
(I^c) or its salts
(I^q) or its salts
Process 11
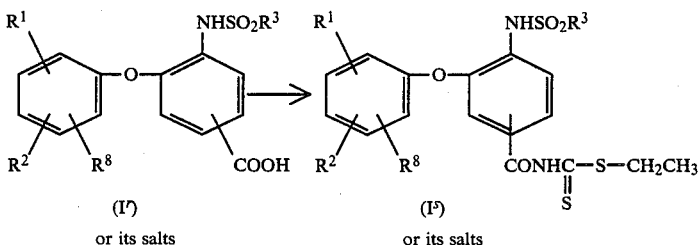
(I^r) or its salts
(I^s) or its salts
Process 12
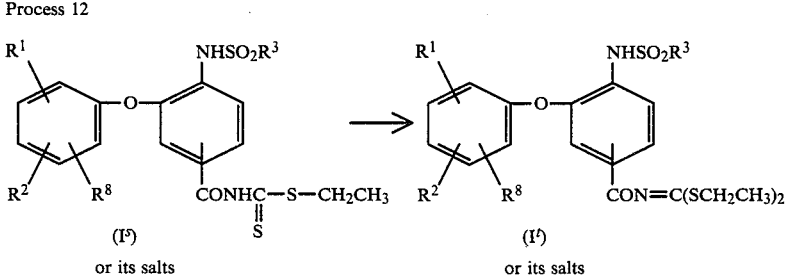
(I^s) or its salts
(I^t) or its salts
Process 13
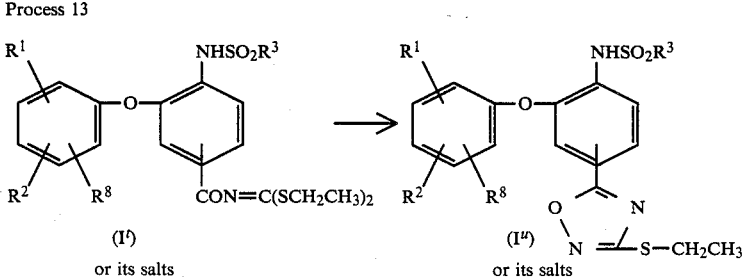
(I^t) or its salts
(I^u) or its salts -continued
Process 14
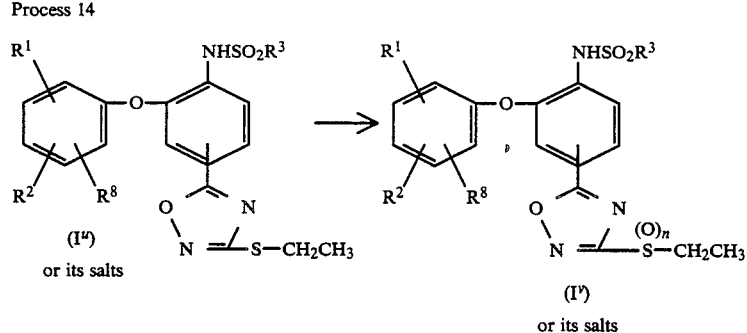
(I$^u$) or its salts → (I$^v$) or its salts
Process 15
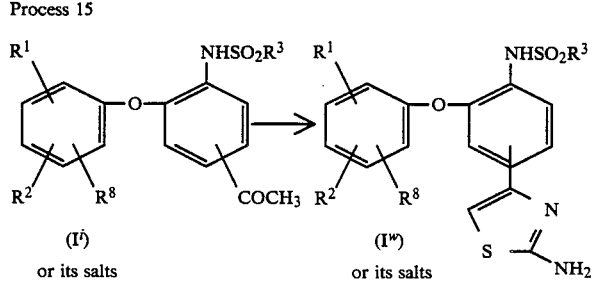
(I$^i$) or its salts → (I$^w$) or its salts
Process 16
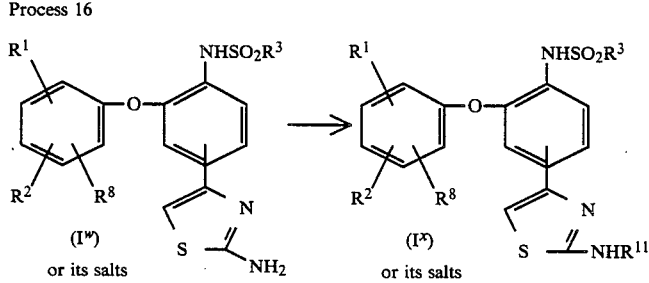
(I$^w$) or its salts → (I$^x$) or its salts
Process 17
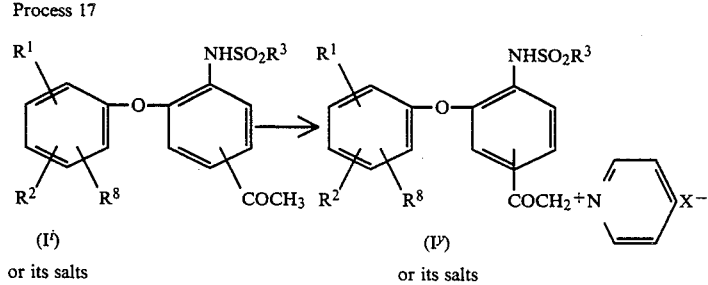
(I$^i$) or its salts → (I$^y$) or its salts
Process 18
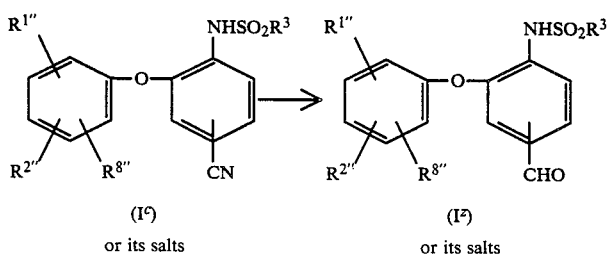
(I$^c$) or its salts → (I$^z$) or its salts Process 19

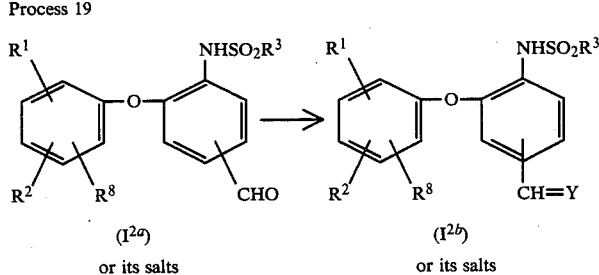

(I²ᵃ)
or its salts (I²ᵇ)
or its salts

Process 20

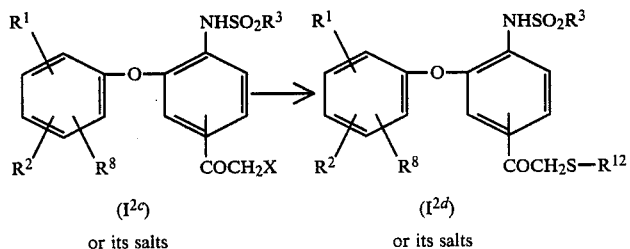

(I²ᶜ)
or its salts (I²ᵈ)
or its salts

Process 21

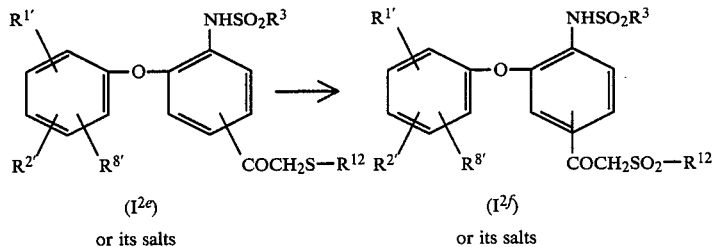

(I²ᵉ)
or its salts (I²ᶠ)
or its salts

Process 22

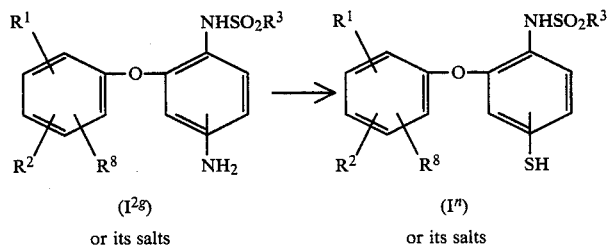

(I²ᵍ)
or its salts (Iⁿ)
or its salts

Process 23

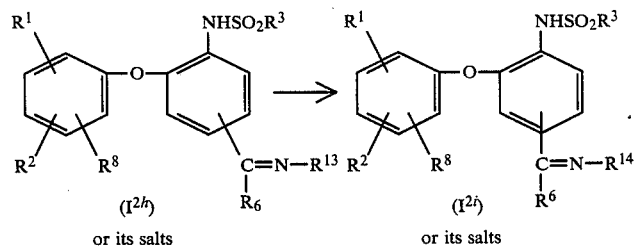

(I²ʰ)
or its salts (I²ⁱ)
or its salts

In the above formulae, $R^{1'}$, $R^{2'}$ and $R^{8'}$ are each the same as defined in $R^1$, $R^2$ and $R^8$ excepting lower alkylthio and lower alkylsulfinyl, $R^{4'}$ is the same as defined in $R^4$ excepting mercapto, lower alkylthio and lower alkylsulfinyl, $R^{4'''}$ is acyl, cyano, lower alkylthio, lower alkylsulfinyl, lower alkylsulfonyl, 5-membered unsaturated heterocyclic group which may have lower alkanoylamino, lower alkylthio or lower alkylsulfonyl, phenylthio which may have nitro, lower alkanoyl(lower)alkenyl, or a group of the formula:

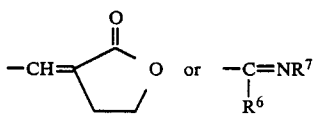

wherein R[6] is hydrogen or lower alkyl and R[7] is lower alkoxy, lower alkoxycarbonyl(lower)alkoxy, ureido or thioureido, R[1''], R[2''] and R[8''] are each the same as defined in R[1], R[2] and R[8] excepting CN, R[9], R[10] and R[12] are each lower alkyl, R[11] is lower alkanoyl, R[13] is lower alkoxycarbonyl(lower)alkoxy, R[14] is carboxy(lower)alkoxy, X is halogen, Y is a group of the formula:

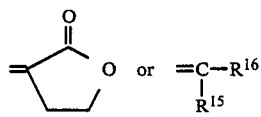

wherein R[15] is hydrogen or lower alkyl, R[16] is lower alkanoyl, n is an integer of 1 or 2, and R[1] to R[8] are each as defined before.

Preferred pharmaceutically acceptable salts of the object compound (I) are conventional non-toxic salts and may include a salt with a base such as a salt with an inorganic base, for example, an alkali metal salt (e.g. lithium salt, sodium salt, potassium salt, etc.), an alkaline earth metal salt e.g. calcium salt, magnesium salt, etc.), an ammonium salt; a salt with an organic base, for example, an organic amine salt (e.g. triethylamine salt, ethanolamine salt, triethanolamine salt, dicyclohexylamine salt, N,N'-dibenzylethylenediamine salt, etc.) and the like.

Preferred examples and illustrations of the various definitions, in the above descriptions, which the present invention includes within the scope thereof are explained in detail as follows.

The term "lower" is intended to mean 1 to 6 carbon atoms, unless otherwise indicated.

Preferred examples of "halogen" is fluorine, chlorine, bromine and iodine.

Preferred examples of "lower alkyl" and the lower alkyl moiety in the term of "hydroxy(lower)alkyl" may include a residue of straight and branched alkane having 1 to 6 carbon atoms such as methyl, ethyl, propyl, isopropyl, butyl, isobutyl, t-butyl, pentyl, neopentyl, hexyl and the like, and preferably the one having 1 to 4 carbon atom(s).

Preferred examples of "lower alkoxy" and the lower alkoxy moiety in the term of "carboxy(lower)alkoxy" may include a straight or branched one such as methoxy, ethoxy, propoxy, isopropoxy, butoxy, isobutoxy, tert-butoxy, pentyloxy, hexyloxy or the like, in which the preferable one is $C_1$-$C_4$ alkoxy and the most preferable one is methoxy or ethoxy.

Preferred example of "halo(lower)alkyl" may include those groups which are derived from the groups given above as preferred examples of the "lower alkyl" by substitution with one or more fluorine, chlorine, bromine and/or iodine optionally on one or more carbon atoms thereof. A most preferred example of such group is trifluoromethyl, for instance.

Preferred examples of "mono or di- lower alkylamino" may include mono or di- lower alkylamino in which the lower alkyl moiety is the same as those given above as preferred examples of the "lower alkyl". More preferred examples of such group may include methylamino, ethylamino, dimethylamino, diethylamino and the like.

Preferred examples of "lower alkylthio" may include methylthio, ethylthio, propylthio, isopropylthio, butylthio and the like, and preferably the one having 1 to 4 carbon atoms.

Preferred examples of "lower alkylsulfinyl" may include methylsulfinyl, ethylsulfinyl, propylsulfinyl, isopropylsulfinyl, butylsulfinyl and the like, and preferably the one having 1 to 4 carbon atoms.

Preferred examples of "lower alkylsulfonyl" may include mesyl, ethylsulfonyl, propylsulfonyl, isopropylsulfonyl, butylsulfonyl and the like, preferably the one having 1 to 4 carbon atoms.

Preferred examples of "lower alkanoyl" may include the same as those exemplified in the explanation of "acyl" hereinafter, and preferably the one having 1 to 4 carbon atoms.

Preferred examples of "lower alkanoyl(lower)alkenyl" may include lower alkenyl (e.g. vinyl, allyl, 1-propenyl, 1 or 2 or 3-butenyl), optional carbon atom(s) of which are substituted with lower alkanoyl (e.g. formyl, acetyl, propionyl, butyryl, isobutyryl, etc.).

Preferred examples of "lower alkoxycarbonyl(lower)alkoxy" may include lower alkoxy (e.g. methoxy, ethoxy, propoxy, isopropoxy, butoxy, isobutoxy, tert-butoxy, pentoxy, etc.), optional carbon atom(s) of which are substituted with lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentoxycarbonyl, etc.).

Preferred examples of 5-membered unsaturated heterocyclic group moiety of "5-membered unsaturated heterocyclic group which may have amino, lower alkanoylamino, lower alkylthio of lower alkylsulfonyl" may include the 5-membered unsaturated heterocyclic group containing nitrogen atom(s), sulfur atom(s) and (or) oxygen atom(s), such as 4-thiazolyl, 1H-5-tetrazolyl, 1,2,4-oxadiazol-5-yl and the like.

Preferred examples of "acyl" may include alkanoyl such as straight or branched lower alkanoyl [e.g. formyl, acetyl, propionyl, butyryl, isobutyryl, valeryl, isovaleryl, pivaloyl, hexanoyl, 3,3-dimethylbutyryl, etc.] or higher alkanoyl [e.g. heptanoyl, octanoyl, myristoyl, palmitoyl, stearoyl, etc.], straight or branched lower alkenoyl [e.g. acryloyl, crotonoyl, isocrotonoyl, 3-butenoyl, methacryloyl, etc.], carbamoyl, mono or di-(lower)alkylcarbamoyl [e.g. methylcarbamoyl, N,N-dimethylcarbamoyl, ethylcarbamoyl, propylcarbamoyl, isopropylcarbamoyl, butylcarbamoyl, isobutylcarbamoyl, tert-butylcarbamoyl, etc.], mono or di- (lower)alkoxycarbamoyl (e.g. methoxycarbamoyl, N,N-dimethoxycarbamoyl, ethoxycarbamoyl, propoxycarbamoyl, etc.), lower alkylthio(lower)alkanoyl (e.g. methylthioacetyl, ethylthioacetyl, etc.), lower alkylsulfonyl(lower)alkanoyl (e.g. methylsulfonylacetyl, ethylsulfonylacetyl, etc.), S-lower alkylisothioureidocarbonyl (e.g. S-ethylisothioureidocarbonyl, etc , lower alkylthiothiocarbonylcarbamoyl (e.g. ethylthiothiocarbonylcarbamoyl, etc.), di(lower alkylthio)methyleneaminocarbonyl, [e.g. di(ethylthio)methyleneaminocarbonyl, etc.], lower alkanoylcarbonyl (e.g. pyruvoyl, etc.), lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexyloxycarbonyl, etc.], mono- or di- or trihalo(lower)alkanoyl [e.g.

chloroformyl, chloroacetyl, bromoacetyl, trifluoroacetyl, etc.], lower alkylamino-(lower)alkanoyl [e.g. methylaminoacetyl, ethylaminoacetyl, propylaminoacetyl, etc.], amino(lower)alkanoyl [e.g. aminoacetyl, aminopropionyl, etc.], aroyl [e.g. benzoyl, toluoyl, xyloyl, naphthoyl, etc.], 6-membered saturated heterocyclic-carbonyl containing nitrogen atom(s) (e.g. 4-methyl-1-piperazinylcarbonyl, etc.], 6-membered unsaturated heterocyclic containing nitrogen atom(s) (lower)alkanoyl (e.g. pyridinioacetyl, etc.), and the like.

Processes for preparing the object compound (I) or its salts of this invention are explained in detail in the following.

Process 1

The object compound (I') or its salts can be prepared by reacting a compound (II) or its salts with a sulfonylating agent.

Suitable salts of the compounds (I') and (II) may include the same as those exemplified as pharmaceutically acceptable salts of the compound (I) hereinbefore.

Suitable sulfonylating agents are the corresponding sulfonic acid compounds, which are represented by the formula: $R^3SO_2$—OH wherein $R^3$ is as defined before, and reactive derivatives thereof.

As suitable said reactive derivatives, there may be mentioned acid halides, acid anhydrides and the like. Suitable examples of such reactive derivatives are acid halides such as acid chloride and acid bromide, mixed acid anhydrides with various acids [e.g. substituted phosphoric acid such as dialkyl phosphoric acid, sulfuric acid, substituted sulfonic acid such as alkanesulfonic acid, etc.], symmetric acid anhydrides and the like. The kind of such reactive derivatives can be selected depending on the kind of the group to be introduced.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the sulfonic acid compounds are used as sulfonylating agents in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under warming or heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

Process 2

The object compound ($I^b$) or its salts can be prepared by reacting the compound ($I^a$) or its salts with an amine compound of the formula:

$H_2N$—$R^7$ wherein $R^7$ is as defined before, or its salts.

Suitable salts of the compounds ($I^a$) and ($I^b$) may include the same as those exemplified as pharmaceutically acceptable salts of the compound (I) hereinbefore.

Suitable salts of the amine compound may include an inorganic acid salt (e.g. hydrochloride, hydrobromide, sulfate, etc.) and an organic acid salt (e.g. formate, acetate, 2,2,2-trifluoroacetate, p-toluenesulfonate, etc.).

This reaction may be preferably conducted in the presence of a base. Suitable base may be an inorganic base such as alkali or alkaline earth metal hydroxide (e.g. sodium hydroxide, potassium hydroxide, calcium hydroxide, etc.), alkali metal bicarbonate (e.g. sodium bicarbonate, potassium bicarbonate, etc.), alkali or alkaline earth metal carbonate (e.g. sodium carbonate, calcium carbonate, etc.), alkali metal phosphate (e.g. sodium dihydrogenphosphate, potassium dihydrogenphosphate, disodium hydrogenphosphate, dipotassium hydrogenphosphate, etc.) or an organic base such as alkali metal alkoxide (e.g. sodium methoxide, potassium ethoxide, etc.), amines (e.g. triethylamine, pyridine, lutidine, etc.).

The reaction is usually conducted in conventional manner. For example, the reaction is preferably conducted under cooling, at ambient temperature, or under warming or heating in conventional solvent which does not have an adverse influence on the reaction such as water, methanol, ethanol, propanol, N,N-dimethylformamide or an optional mixture thereof.

Process 3

The object compound ($I^d$) or its salts can be prepared by hydrolysing the compound ($I^c$) or its salts.

Suitable salts of the compounds ($I^c$) and ($I^d$) may include the same as those exemplified as pharmaceutically acceptable salts of the compound (I).

In this hydrolysis reaction, all conventional methods used in the hydrolysis of the group "CN" to the group "COOH", are applicable.

The hydrolysis is preferably carried out in the presence of a base or an acid. Suitable bases may include the same as those exemplified in the preceding Process 2.

Suitable acids may include an organic acid (e.g. formic acid, acetic acid, propionic acid, etc.) and an inorganic acid (e.g. hydrochloric acid, hydrobromic acid, sulfuric acid, etc.).

This hydrolysis is usually carried out in an organic solvent, water or a mixed solvent thereof.

The reaction temperature is not critical and the reaction can usually be carried out at ambient temperature or under warming or heating around boiling point of the solvent.

Process 4

The object compound ($I^h$) or its salts can be prepared by oxidizing a compound ($I^g$) or its salts.

Suitable salts of the compounds ($I^h$) and ($I^g$) may include the same as those exemplified as pharmaceutically acceptable salts of the compound (I) hereinbefore.

This oxidation reaction can be carried out by a conventional method which is applied for the transformation of —S— into

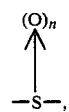

for example by using an oxidizing agent such as m-chloroperbenzoic acid, perbenzoic acid, peracetic acid, ozone, hydrogen peroxide, periodic acid or the like.

This reaction is usually carried out in a solvent such as water, acetone, dioxane, acetonitrile, chloroform, dichloromethane, tetrahydrofuran, ethyl acetate or any other solvent which does not adversely affect the reaction.

The reaction temperature is not critical and the reaction is preferably carried out under cooling or at ambient temperature.

Process 5

The object compound ($I^j$) or its salts can be prepared by reducing a compound ($I^i$) or its salts.

Suitable salts of the compounds ($I^i$) and ($I^j$) may include the same as those exemplified as pharmaceutically acceptable salts of the compound (I) hereinbefore.

The reduction is conducted by a conventional method such as a catalytic reduction; a reduction using a combination of a metal such as iron, tin or zinc and an acid such as an inorganic acid (hydrochloric acid, sulfuric acid or the like) or an organic acid (acetic acid or the like); a combination of an alloy (e.g., sodium amalgam, aluminum amalgam, etc.), a metal (e.g., zinc, tin, iron, etc.) or a salt thereof (e.g., zinc chloride, stannous chloride, ferrous chloride, etc.) and water, an alkali solution or an alcohol (e.g., methanol, ethanol, propanol or butanol); a hydrazine compound (e.g., phenyl hydrazine or hydrazine); a combination of titanium chloride and hydrochloric acid; an alkali metal borohydride such as sodium borohydride, and potassium borohydride; lithium aluminum hydride; diborane, borane; or an electrolytic reduction.

Suitable examples of catalysts for the catalytic reduction are conventional ones.

In this reduction process, optically active compounds as an object compound ($I^j$) can be obtained by using as a reducing agent a combination of the above reducing agent and optically active ligands such as 4-anilino-3-methylamino-1-butanol, 2-amino-1,1-diphenyl-3-methylbutan-1-ol and the like.

The reaction conditions for this reduction, for example, the solvent to be used and the reaction temperature may optionally be selected in accordance with the reduction method to be used. In general, it is preferable to employ a solvent such as water, an alcohol such as methanol, ethanol and propanol, dioxane, acetonitrile, tetrahydrofuran, dimethylformamide, pyridine and the like.

The reaction temperature is not particularly limited and the reaction is usually conducted under cooling, at ambient temperature or at an elevated temperature.

Process 6

The object compound [$I^k$] or its salts can be prepared by reacting a compound [$I^c$] or its salts with a hydroxylamine or its salt.

Suitable salts of the compounds ($I^c$) and ($I^k$) may include the same as those exemplified as pharmaceutically acceptable salts of the compound (I) hereinbefore.

Suitable salts of the hydroxylamine may include an inorganic acid salt (e.g. hydrochloride, hydrobromide, sulfate, etc.) and an organic acid salt (e.g. formate, acetate, 2,2,2-trifluoroacetate, p-toluenesulfonate, etc.).

This reaction may preferably be conducted in the presence of a base. Suitable bases may include the same as those exemplified as a suitable base in the explanation of Process 2.

The reaction is usually conducted in a conventional manner. For example, the reaction is preferably conducted under cooling, at ambient temperature, or under warming or heating in a conventional solvent which does not have an adverse influence on the reaction such as water, methanol, ethanol, propanol, N,N-dimethylformamide or an optional mixture thereof.

Process 7

The object compound ($I^m$) or its salts can be prepared by oxidizing a compound ($I^l$) or its salts.

Suitable salts of the compounds ($I^m$) and ($I^l$) may include the same as those exemplified as pharmaceutically acceptable salts of the compound (I) hereinbefore.

This reaction is conducted substantially in the same manner as that of Process 4, and is to be referred thereto.

Process 8

The object compound ($I^o$) or its salts can be prepared by reacting a compound ($I^n$) or its salt with halonitrobenzene.

Suitable salts of the compounds ($I^o$) and ($I^n$) may include the same as those exemplified as pharmaceutically acceptable salts of the compound (I) hereinbefore.

This reaction may preferably be conducted in the presence of a base.

Suitable bases may include the same as those exemplified as a suitable base in the explanation of Process 2.

The reaction is usually conducted in a conventional manner. For example, the reaction is preferably conducted at ambient temperature, or under warming or heating in a conventional solvent which does not have an adverse influence on the reaction, such as benzene, toluene, xylene, N,N-dimethylformamide, dioxane, acetone, chloroform or the like.

Process 9

The object compound ($I^p$) or its salts can be prepared by reducing a compound ($I^o$) or its salts.

Suitable salts of the compound ($I^o$) and ($I^p$) may include the same as those exemplified as pharmaceutically acceptable salts of the compound (I) hereinbefore.

The reduction is carried out substantially in the same manner as that of Process 5, and is to be referred thereto.

Process 10

The object compound ($I^q$) or its salts can be prepared by reacting a compound ($I^c$) or its salts with alkali metal or ammonium azide and an inorganic salts.

Suitable salts of the compounds ($I^q$) and ($I^c$) may include the same as those exemplified as pharmaceutically acceptable salts of the compound (I) hereinbefore.

Preferred examples of alkali metal azide may include sodium azide, potassium azide and the like, and preferred examples of an inorganic salt may include ammonium halide such as ammonium chloride, ammonium bromide and the like.

The reaction is usually carried out at ambient temperature, or under warming or heating in a conventional solvent which does not have an adverse influence on the reaction, such as methanol, ethanol, dioxane, dimethylformamide, tetrahydrofuran and the like.

Process 11

The object compound ($I^s$) or its salts can be prepared by following 3 steps:
(1) the first step: reacting a compound ($I^r$) or its salt with phosphorus pentachloride, thionyl chloride or the like,
(2) the 2nd step: reacting the resulting compound with potassium thiocyanate, sodium thiocyanate, ammonium thiocyanate, lead thiocyanate or the like,
(3) the 3rd step: reacting the resulting compound with ethyl mercaptan.

Suitable salts of the compounds ($I^s$) and ($I^r$) may include the same as those exemplified as pharmaceutically acceptable salts of the compound (I) hereinbefore.

The reaction of the first step is usually carried out under cooling, at ambient temperature, or under warming or heating in a conventional solvent which does not have an adverse influence on the reaction, such as benzene, toluene, xylene, chloroform, methylene chloride or the like.

The reactions of the 2nd and 3rd steps are usually carried out at ambient temperature, or under warming or heating in a conventional solvent which does not have an adverse influence on the reaction, such as benzene, toluene, xylene, dioxane, acetonitrile or the like.

Process 12

The object compound ($I^t$) or its salts can be prepared by reacting a compound ($I^s$) or its salts with ethyl halide.

Suitable salts of the compounds ($I^t$) and ($I^s$) may include the same as those exemplified as pharmaceutically acceptable salts of the compound (I) hereinbefore.

The reaction may preferably be conducted in the presence of a base and suitable examples of the base may include the same as those exemplified as a suitable base in the explanation of Process 2.

The reaction is usually conducted under cooling or at ambient temperature in a conventional solvent which does not have adverse influence on the reaction, such as an alcohol (e.g. methanol, ethanol, etc.), ether, dioxane, tetrahydrofuran or the like.

Process 13

The object compound ($I^u$) or its salts can be prepared by reacting a compound ($I^t$) or its salts with hydroxylamine or its salt.

Suitable salts of the compounds ($I^u$) and ($I^t$) may include the same as those exemplified as pharmaceutically acceptable salts of the compound (I) hereinbefore.

Suitable salts of hydroxylamine may include the same as those exemplified as suitable salts of the amine compound in the explanation of Process 2.

The reaction may preferably be carried out in the presence of a base, and suitable bases may include the same as those exemplified as a suitable base in the explanation of Process 2.

The reaction is usually carried out at ambient temperature, or under warming or heating in a conventional solvent which does not have an adverse influence on the reaction, such as methanol, ethanol, isopropanol or the like.

Process 14

The object compound ($I^v$) or its salts can be prepared by oxidizing a compound ($I^u$) or its salts.

Suitable salts of the compounds ($I^v$) and ($I^u$) may include the same as those exemplified as pharmaceutically acceptable salts of the compound (I) hereinbefore.

This reaction is conducted substantially in the same manner as that of Process 4, and is to be referred thereto.

Process 15

The object compound ($I^w$) or its salts can be prepared by the following 2 steps:
(1) the first step: reacting a compound ($I^t$) or its salt with a halogenating agent such as halogen (e.g. chlorine, bromine, etc.), halosuccinimide (e.g. N-bromosuccinimide, N-chlorosuccinimide, etc.), sulfuryl chloride or the like,
(2) the 2nd step: reacting the resulting compound with thiourea.

The reaction of the first step is carried out under cooling, at ambient temperature, or under warming or heating in a conventional solvent which does not have an adverse influence on the reaction, such as chloroform, methylene chloride, benzene, toluene, xylene or the like.

The reaction may preferably be conducted in the presence of a reaction initiator such as benzoyl peroxide or the like.

The reaction of the 2nd step is usually carried out at ambient temperature, or under warming or heating in a conventional solvent which does not have an adverse influence on the reaction, such as methanol, ethanol, dimethylformamide, dioxane, tetrahydrofuran, chloroform or the like.

Process 16

The object compound ($I^x$) or its salts can be prepared by reacting a compound ($I^w$) or its salts with a compound of the formula: $R^{11}$—OH, wherein $R^{11}$ is as defined before, or its reactive derivative.

Suitable salts of the compounds ($I^x$) and ($I^w$) may include the same as those exemplified as pharmaceutically acceptable salts of the compound (I) hereinbefore.

Suitable reactive derivatives may include acid anhydride, acid halide, activated ester, activated amide or the like.

The reaction may be carried out in the presence or absence of a base and suitable bases may include the same as those exemplified as a suitable base in the explanation of Process 2.

The reaction is usually carried out under cooling, at ambient temperature, or under warming or heating in the presence or absence of a conventional solvent which does not have an adverse influence on the reaction, such as tetrahydrofuran, dioxane, chloroform, methylene chloride, ethyl acetate or the like.

Process 17

The object compound ($I^y$) or its salts can be prepared by reacting a compound ($I^t$) or its salts with a halogenating agent and then pyridine.

Suitable salts of the compounds ($I^y$) and ($I^t$) may include the same as those exemplified as pharmaceutically acceptable salts of the compound (I) hereinbefore.

Suitable halogenating agents may include the same as those exemplified in the explanation of the first step of Process 15.

The reaction is usually carried out at ambient temperature, or under warming or heating in a conventional solvent which does not have are adverse influence on the reaction, such as methylene chloride, chloroform, dioxane, methanol, ethanol or the like.

Process 18

The object compound ($I^z$) or its salts can be prepared by reducing a compound ($I^c$) or its salts.

Suitable salts of the compounds ($I^z$) and ($I^c$) may include the same as those exemplified as pharmaceutically acceptable salts of the compound (I) hereinbefore.

Suitable reducing agents may include Raney's nickel, lithium aluminum hydride, lithium triethoxy aluminum hydride, sodium triethoxyaluminum hydride, diisobutyl aluminum hydride or the like.

The reaction is usually carried out under cooling, at ambient temperature, or under warming or heating in a solvent which does not have an adverse influence on the reaction, such as aqueous formic acid solution (in case of use of Raney's nickel), ether, tetrahydrofuran or the like.

Process 19

The object compound ($I^{2b}$) or its salts can be prepared by reacting a compound ($I^{2a}$) or its salts with a compound of the formula: $Y=P(Ph)_3$.

Suitable salts of the compounds ($I^{2b}$) and ($I^{2a}$) may include the same as those exemplified as pharmaceutically acceptable salts of the compound (I) hereinbefore.

This reaction is usually carried out in a solvent such as dimethyl sulfoxide, dioxane, acetonitrile, chloroform, dichloromethane, tetrahydrofuran, dimethylformamide, ethyl acetate, or any other solvent which does not adversely affect the reaction.

The reaction temperature is not critical and the reaction is usually carried out at ambient temperature, or under warming or heating.

Process 20

The object compound ($I^{2d}$) or its salts can be prepared by reacting a compound ($I^{2c}$) or its salts with a compound of the formula: $R^{12}$—SH, wherein $R^{12}$ is as defined before.

Suitable salts of the compounds ($I^{2d}$) and ($I^{2c}$) may include the same as those exemplified as pharmaceutically acceptable salts of the compound (I) hereinbefore.

The reaction is usually carried out under cooling, at ambient temperature or under warming or heating in a solvent which does not have an adverse influence on the reaction, such as alcohol (e.g. methanol, ethanol, etc.), chloroform, methylene chloride, dioxane or the like.

Process 21

The object compound ($I^{2f}$) or its salts can be prepared by oxidizing a compound ($I^{2e}$) or its salts.

Suitable salts of the compounds ($I^{2f}$) and ($I^{2e}$) may include the same as those exemplified as pharmaceutically acceptable salts of the compound (I) hereinbefore.

This reaction is conducted substantially in the same manner as that of Process 4, and is to be referred thereto.

Process 22

The object compound ($I^n$) or its salt can be prepared by the following 3 steps:
(1) the first step: reacting a compound ($I^{2g}$) with nitrous acid or its salts,
(2) the 2nd step: reacting the resulting compound with potassium O-ethyl dithiocarbonate,
(3) the 3rd step: hydrolyzing the resulting compound in the presence of a base.

Suitable salts of the compounds ($I^n$) and ($I^{2g}$) may include the same as those exemplified as pharmaceutically acceptable salts of the compound (I) hereinbefore.

Suitable salts of nitrous acid may include the same as those exemplified as pharmaceutically acceptable salts of the compound (I) hereinbefore.

The reaction of the first step is usually carried out under cooling or at ambient temperature in a solvent which does not have an adverse influence on the reaction, such as water, methanol, ethanol, propanol or the like.

The reaction of the 2nd step is usually carried out at room temperature, or under warming or heating in a solvent which does not have an adverse influence on the reaction, such as water, methanol, ethanol, propanol or the like.

The reaction of the 3rd step is usually carried out under cooling, at ambient temperature or under warming in a solvent which does not have an adverse influence on the reaction, such as water, methanol, ethanol, propanol or the like.

Suitable bases may include the same as those exemplified as a suitable base in the explanation of Process 2.

Process 23

The object compound ($I^{2i}$) or its salts can be prepared by subjecting a compound ($I^{2h}$) or its salts to hydrolysis.

Suitable salts of the compounds ($I^{2i}$) and ($I^{2h}$) may include the same as those exemplified as pharmaceutically acceptable salts of the compound (I) hereinbefore.

The hydrolysis is preferably conducted in the presence of an acid or a base.

Preferred examples of the acid may include inorganic acids (e.g. hydrochloric acid, hydrobromic acid, sulfuric acid, etc.), organic acid (e.g. formic acid, acetic acid, trifluoroacetic acid, propionic acid, benzenesulfonic acid, p-toluenesulfonic acid, etc.), and acidic ion-exchange resins.

Preferred examples of the base may include the same as those exemplified as a suitable base in the explanation of Process 2.

The hydrolysis is conducted under comparatively mild conditions, under cooling or warming, in a solvent which does not have an adverse influence on the reaction, such as water, alcohol (e.g. methanol, ethanol, propanol, etc.), acetone, N,N-dimethylformamide, tetrahydrofuran, dioxane, dimethyl sulfoxide or a mixture thereof, benzene or diethyl ether, etc. Among them, those acids or bases which are liquid may serve also as solvents.

As to the above-mentioned Processes 1 to 23, in case that the object compounds are obtained as these free compounds, these object compounds can be obtained as these salts by treating these free compounds with a base, suitable examples of which may include the same as those exemplified in the explanation of Process 2.

The starting compound (II) and its salts are novel and can be prepared, for example, according to Preparations as illustrated hereinafter or a similar manner thereto.

The object compound, alkanesulfonanilide derivatives (I) and pharmaceutically acceptable salts thereof of this invention are novel compounds which have antiinflammatory activities, analgesic activities and antipyretic activities, and useful as antiinflammatory (including rheumatic, arthritic) agents, analgesic agents or antipyretic agents for human being and animals.

In order to illustrate the usefulness of the object compound (I), the pharmacological test data of the representative compound of the object compound (I) are shown below.

Anti-inflammatory activity

Test 1

Effect on adjuvant arthritis in rats

Method

Ten female Sprague-Dawley rats were used per group. A dose of 0.5 mg of Mycobacterium tuberculosis (strain Aoyama B) suspended in 0.05 ml of liquid paraffin was injected subcutaneously in the right hind paw. The injection of mycobacterial adjuvant produced local inflammatory lesions (primary lesion) and then about 10 days later, secondary lesions in both the injected and unijected paws. The difference in volumes of both paws before and after adjuvant injection was the measure of arthritis. The drug was given orally once a day for 23 consecutive days from day 1.

| | Results | |
|---|---|---|
| Compound (Example No.) | Dose level (mg/kg) | Inhibition of Secondary Lesion (uninjected paw; %) |
| Example 1 | 1.0 | 50.0 |
| Example 3 | 3.2 | 66.0 |
| Example 14 | 3.2 | 59.4 |
| Example 16 | 3.2 | 62.5 |
| Example 20 | 1.0 | 49.3 |
| Example 25 | 10.0 | 81.6 |
| Example 32 | 10.0 | 63.4 |
| Example 40 | 10.0 | 70.4 |
| Ibuprofen | 10.0 | 24.7 |
| Ibuprofen | 100.0 | 79.4 |

Analgesic activity

Test 2

Writhing syndrome induced by acetic acid in mice

Method

Ten male ddY mice were used per group. Writhing syndrome was produced by an intraperitoneal injection of 20 ml/kg of 0.6% acetic acid in mice. The animals were observed from 3 to 13 minutes after acetic acid injection, and a total number of writhing episodes was recorded. The drugs were given orally 1 hour before acetic acid injection. The frequency of writhing in the treated animals was compared with that in the control animals.

| | Results |
|---|---|
| Compound (Example No.) | $ED_{50}$ (mg/kg) |
| Example 1 | 14.0 |
| Example 3 | 2.4 |
| Example 20 | 55.8 |
| Example 25 | 9.6 |
| Example 40 | 18.0 |
| Indomethacin | 1.6 |

Anti-pyretic activity

Test 3

Method

Ten male Sprague-Dawley rats were used per group. Pyrexia was induced by SC injection of 10 ml/kg of 5% brewer's yeast suspension. The drugs were given orally hours after yeast injection. Rectal temperature was measured 1 and 2 hours after administration of drugs, and the difference of rectal temperature from that before yeast injection was calculated.

| | Results | |
|---|---|---|
| Compound | $ED_{50}$ (mg/kg) | |
| (Example No.) | 1 hr | 2 hr |
| Example 1 | 10.0 | 6.8 |
| Indomethacin | 4.6 | 2.6 |

Anti-inflammatory activity

Test 4

Effect on adjuvant arthritis in rats

Method: The same as that of Test 1

| | Results | |
|---|---|---|
| Compound (Example No.) | Dose level (mg/kg) | Inhibition of Secondary Lesion (uninjected paw 1%) |
| Example 73 | 0.32 | 59.0 |
| | 1.0 | 81.3 |
| Naproxen | 0.32 | 37.0 |
| | 3.2 | 67.1 |

Analgesic activity

Test 5

Inflammatory hyperalgesia induced by brewer's yeast in rats

Method

Ten male Sprague Dawley rats were used per group. 0.1 Ml of 5% brewer's yeast suspended in 0.5% methylcellulose was injected into the right hind paw, The pain threshold was determined 3 hours after yeast injection, by applying pressure to the foot and reading the pressure at which the rat withdrew the foot.

The drugs were given orally 2 hours after yeast infection. The pain threshold in the treated animals was compared with that in the control animals.

| | Result |
|---|---|
| Compound Example No. | $ED_{30}$ (mg/kg) |
| Example 73 | 1.8 |
| Indomethacin | 5.1 |

Pharmaceutical compositions of this invention can be used in a conventional pharmaceutical forms such as powders, fine granules, granules, tablets, dragee, microcapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweetning agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 50 mg to 5 g as the object compound (I) or its pharmaceutically acceptable salts, preferably 100 mg to 500 mg on the same basis, at the interval of 1 to 3 times a day. Typical unit doses may be 50 mg, 100 mg, 200 mg, 500 mg, 1 g and the like, although these are only examples and not limitative, of course.

The following Examples are given for the purpose of illustrating this invention.

PREPARATION 1

A mixture of p-aminoacetophenone (20 g), pyridine (11.7 g), and iodobenzene dichloride (40 g) in tetrahydrofuran (300 ml) was stirred for 5 hours at 0° C. The insoluble materials were filtered, and the filtrate was concentrated under reduced pressure. The residue obtained was crystallized from ethanol to give colorless crystals of 4'-amino-3'-chloroacetophenone (20.1 g).

IR (Nujol): 3420, 3340, 3230, 1665, 1635, 1590 cm$^{-1}$.

PREPARATION 2

A solution of sodium nitrite (1.63 g) in water (4.3 ml) was added dropwise to a solution of 4'-amino-3'-chloroacetophenone (2.5 g) and concentrated hydrochloric acid (5.5 ml) in water (5.5 ml) at 0° to 3° C., and the solution was stirred for 15 minutes at 0° C. The resulting solution was added portionwise to a mixture of sodium nitrite (7.3 g) and cuprous oxide (0.76 g) in water (32 ml) at −5° to 0° C. The mixture was stirred for 1 hour at 0° C. and for 1 hour at room temperature, and extracted with chloroform. The extract was washed with a saturated aqueous solution of sodium chloride, dried over magnesium sulfate, and concentrated under reduced pressure. The residue was subjected to column chromatography on silica gel (60 g) eluting with chloroform. The fractions containing the desired compound were combined and concentrated under reduced pressure to give pale yellow crystals of 3'-chloro-4'-nitroacetophenone (2.2 g).

mp: 47° to 49° C.
IR (Nujol): 1695, 1580, 1530, 1360 cm$^{-1}$.
NMR (CDCl$_3$, δ): 2.66 (3H, s), 7.8–8.2 (3H, m).
MASS (m/e): 199 (M$^+$), 184 (base).

PREPARATION 3

A mixture of 3'-chloro-4'-nitroacetophenene (3 g), 2,4-difluorophenol (2.4 g) and potassium carbonate (2.5 g) in xylene (70 ml) was stirred for 14 hours at 150° C. The insoluble materials were filtered and the filtrate was concentrated under reduced pressure. The residue obtained was triturated with ethanol to give crystals of 3'-(2,4-difluorophenoxy)-4'-nitroacetophenone (2.6 g).

mp: 96° to 98° C.
IR (Nujol): 1695, 1610, 1520, 1505 cm$^{-1}$.
NMR (CDCl$_3$, δ): 2.57 (3H, s), 6.8–8.2 (6H, m).
MASS (m/e): 293 (M$^+$), 278.

PREPARATION 4

A mixture of 3'-(2,4-difluorophenoxy)-4'-nitroacetophenone (2.5 g), iron powder (2.5 g) and ammonium chloride (0.25 g) in ethanol (40 ml) and water (20 ml) was refluxed with stirring for 30 minutes. The insoluble materials were filtered and the filtrate was concentrated under reduced pressure. The residue was dissolved in ethyl acetate, washed with a saturated aqueous solution of sodium chloride, dried over magnesium sulfate, and concentrated to give a powder of 4'-amino-3'-(2,4-difluorophenoxy)acetophenone (2.2 g).

mp: 113° to 115° C.
IR (Nujol): 3520, 3380, 1660, 1625, 1595, 1500 cm$^{-1}$.

PREPARATION 5

A mixture of p-aminopropiophenone (5 g), pyridine (2.7 g), and iodobenzene dichloride (7.5 g) in tetrahydrofuran (150 ml) was stirred for 3 hours at 0° to 5° C. The insoluble materials were filtered, and the filtrate was concentrated under reduced pressure. The residue was dissolved in chloroform, washed with an aqueous solution of sodium hydrogen sulfite, dried over magnesium sulfate, and concentrated to give an oil (8.8 g). The oil was subjected to column chromatography on silica gel eluting with chloroform. The fractions containing the desired compound were combined and concentrated under reduced pressure. The residual oil was triturated with a mixture of hexane and ethyl acetate to give pale yellow crystals of 4'-amino-3'-chloropropiophenone (1.1 g).

mp: 79° to 80° C.
IR (Nujol): 3500, 3380, 1670, 1620, 1595 cm$^{-1}$.
NMR (CDCl$_3$, δ): 1.20 (3H, t, J=7 Hz), 2.88 (2H, q, J=7 Hz), 4.50 (2H, broad s), 6.72 (1H, d, J=8 Hz), 7.68 (1H, dd, J=8 Hz, 2 Hz), 7.88 (1H, d, J=2 Hz).
MASS (m/e): 183 (M$^+$), 154 (base peak).

PREPARATION 6

3'-Chloro-4'-nitropropiophenone was prepared according to a similar manner to that of Preparation 2.

IR (Film): 1700, 1585, 1535 cm$^{-1}$.

PREPARATION 7

3'-(2,4-Difluorophenoxy)-4'-nitropropiophenone was prepared according to a similar manner to that of Preparation 3.

mp: 82° to 85° C.
IR (Nujol): 1700, 1610, 1525, 1505 cm$^{-1}$.
NMR (CDCl$_3$, δ): 1.20 (3H, t, J=7 Hz), 2.92 (2H, q, J=7 Hz), 6.8–8.1 (6H, m).

PREPARATION 8

4'-Amino-3'-(2,4-difluorophenoxy)propiophenone was prepared according to a similar manner to that of Preparation 4.

IR (Nujol): 3530, 3390, 1660, 1630, 1595, 1570, 1505 cm$^{-1}$.

PREPARATION 9

An aqueous solution (200 ml) of calcium hypochlorite (21 g) was added to a solution of p-cyanoacetanilide (12.5 g) in ethanol (27 ml), acetic acid (27 ml), and water (27 ml). The mixture was stirred for 4 days and extracted with chloroform. The organic layer was washed with a saturated aqueous solution of sodium chloride, dried over magnesium sulfate, and concentrated to give a powder of 2'-chloro-4'-cyanoacetanilide (12.5 g).

A mixture of 2'-chloro-4'-cyanoacetanilide (12.5 g) and concentrated hydrochloric acid (10 ml) in ethanol (50 ml) was refluxed for 30 minutes, and concentrated under reduced pressure. The residue was dissolved in water, adjusted to pH 9 with 4N-sodium hydroxide aqueous solution, and extracted with chloroform. The extract was concentrated and the residue was subjected to column chromatography on silica gel (150 g) eluting with chloroform. The fractions containing the desired compound were combined and concentrated to give a powder of 4-amino-3-chlorobenzonitrile (5.7 g).

IR (Nujol): 3500, 3380, 2230, 1635, 1600, 1510, 1460 cm$^{-1}$.

PREPARATION 10

3-Chloro-4-nitrobenzonitrile was prepared according to a similar manner to that of Preparation 2.

IR (Nujol): 2250, 1570, 1535 cm$^{-1}$.

PREPARATION 11

3-(2,4-Difluorophenoxy)-4-nitrobenzonitrile was prepared according to a similar manner to that of Preparation 3.

IR (Nujol): 2250, 1615, 1590, 1530, 1510 cm$^{-1}$.

PREPARATION 12

4-Amino-3-(2,4-difluorophenoxy)benzonitrile was prepared according to a similar manner to that of Preparation 4.

IR (Nujol): 3520, 3380, 2220, 1625, 1520, 1500 cm$^{-1}$.

PREPARATION 13

A mixture of 3-(2,4-diflourophenoxy)-4-nitrobenzonitrile (1 g) and potassium hydroxide (0.26 g) in tert. butanol (10 ml) was stirred for 2 minutes at 80° C. The insoluble potassium hydroxide was filtered off and the filtrate was concentrated under reduced pressure. The residue obtained was triturated with diluted aqueous sulfuric acid to give a pale brown powder of 3-(2,4-difluorohenoxy)-4-nitrobenzamide (1 g).

mp: 159° to 163° C.

IR (Nujol): 3530, 3400, 3200, 1680, 1615, 1590, 1535, 1505 cm$^{-1}$.

NMR (CDCl$_3$+CD$_3$OD, δ): 6.8–8.1 (6H, m).

MASS (m/e): 294 (M+).

PREPARATION 14

A mixture of 3-(2,4-difluorophenoxy)-4-nitrobenzamide (1 g), iron powder (1 g), and ammonium chloride (0.1 g) in ethanol (20 ml) and water (10 ml) was refluxed with stirring for an hour. The insoluble materials were filtered off and the filtrate was concentrated under reduced pressure to give pale yellow crystals of 4-amino-3-(2,4-difluorophenoxy)benzamide (0.82 g).

mp: 171° to 173° C.

IR (Nujol): 3400, 3200, 1650, 1620, 1580, 1505, 1445 cm$^{-1}$.

PREPARATION 15

A mixture of 3-(2,4-difluorophenoxy)-4-nitrobenzonitrile (5 g) and concentrated sulfuric acid (5 ml) in water (5 ml) was stirred for 30 minutes at 170° C. Ice-water (80 ml) was added thereto and precipitates were filtered, washed with water and dried. The precipitates (5 g) were dissolved in ethyl acetate, and the insoluble materials were removed by filtration. The filtrate was concentrated under reduced pressure and the residual oil was triturated with hexane to give pale brown crystals of 3-(2,4-difluorophenoxy)-4-nitrobenzoic acid (4.3 g).

mp: 182° to 184° C.

IR (Nujol): 1700, 1615, 1595, 1540, 1505 cm$^{-1}$.

PREPARATION 16

A mixture of 3-(2,4-difluorophenoxy)-4-nitrobenzoic acid (1 g) and phosphorus pentachloride (0.74 g) in benzene (10 ml) was stirred for 30 minutes at room temperature. Benzene was evaporated under reduced pressure to give an oil of 3-(2,4-difluorophenoxy)-4-nitrobenzoyl chloride (1.1 g).

IR (Film): 1750, 1610, 1535, 1505 cm$^{-1}$.

PREPARATION 17

A solution of 3-(2,4-difluorophenoxy)-4-nitrobenzoyl chloride (1.1 g) in dry ether (15 ml) was added dropwise to a stirred mixture of methylamine (40% in water; 2 ml) in water (8 ml) and ether (5 ml) at 5° to 8° C. The mixture was stirred for 30 minutes at 5° C. and for 30 minutes at room temperature. Precipitates in the mixture were filtered and washed with water and ether successively to give pale brown crystals of N-methyl-3-(2,4-difluorophenoxy)-4-nitrobenzamide (0.88 g).

mp: 186° to 188° C.

IR (Nujol): 3350, 1650, 1615, 1590, 1555, 1505 cm$^{-1}$.

NMR (CDCl$_3$+CD$_3$OD, δ): 2.91 (3H, s), 6.8–8.1 (6H, m).

PREPARATION 18

A mixture of N-methyl-3-(2,4-difluorophenoxy)-4-nitrobenzamide (0.85 g), iron powder (0.8 g) and ammonium chloride (80 mg) in ethanol (20 ml) and water (10 ml) was refluxed with stirring for an hour. The insoluble materials were filtered, and the filtrate was concentrated under reduced pressure. The residue was dissolved in ethyl acetate, washed with a saturated aqueous solution of sodium chloride, dried over magnesium sulfate, and concentrated to give a powder of N-methyl-4-amino-3-(2,4-difluorophenoxy)benzamide (0.77 g).

IR (Nujol): 3500, 3350, 3220, 1660, 1630, 1550, 1500 cm$^{-1}$.

PREPARATION 19

A mixture of 3-(2,4-difluorophenoxy)-4-nitrobenzoic acid (1.0 g) and sulfuric acid (3 drops) in ethanol (5 ml) was refluxed for 8 hours. Ethanol was evaporated under reduced pressure, and the residue was dissolved in ethyl acetate, washed with a saturated aqueous solution of sodium bicarbonate, dried over magnesium sulfate, and concentrated to give pale brown needles of ethyl 3-(2,4-difluorophenoxy)-4-nitrobenzoate (1.1 g).

mp: 83° to 85° C.

IR (Nujol): 1720, 1620, 1525, 1505 cm$^{-1}$.

NMR (CDCl$_3$, δ): 1.37 (3H, t, J=7 Hz), 4.40 (2H, q, J=7 Hz), 6.7–8.1 (6H, m).

PREPARATION 20

Ethyl 4-amino-3-(2,4-difluorophenoxy)benzoate was prepared according to a similar manner to that of Preparation 18.

IR (Nujol): 3530, 3400, 3230, 1690, 1630, 1605, 1520, 1510 cm$^{-1}$.

PREPARATION 21

A mixture of 3'-chloro-4'-nitroacetophenone (3.0 g), phenol (2.5 g), and potassium carbonate (4.0 g) in xylene (70 ml) was refluxed for 8 hours. The insoluble was filtered off and the filtrate was concentrated under reduced pressure. The oily residue (2.7 g) was subjected to column chromatography on silica gel (70 g) eluting with toluene. The fractions containing the desired compound were combined and concentrated under reduced pressure to give crystals of 4'-nitro-3'-phenoxyacetophenone (1.7 g).

mp: 40° to 47° C.

IR (Nujol): 1690, 1610, 1580, 1520 cm$^{-1}$.

NMR (CDCl$_3$, δ): 2.55 (3H, S), 6.8-8.1 (8H, m).

PREPARATION 22

4'-Amino-3'-phenoxyacetophenone was prepared according to a similar manner to that of Preparation 4.
mp: 47° to 48° C.
IR (Nujol): 3480, 3370, 1655, 1620, 1590, 1565 cm$^{-1}$.
NMR (CDCl$_3$, δ): 2.48 (3H, s), 4.4 (2H, broad s), 6.7-7.8 (8H, m).

PREPARATION 23

3'-(2-Fluorophenoxy)-4'-nitroacetophenone was prepared according to a similar manner to that of Preparation 21.
mp: 79° to 81° C.
IR (Nujol): 1700, 1610, 1520, 1500 cm$^{-1}$.
NMR (CDCl$_3$, δ): 2.57 (3H, s), 7.1-8.2 (7H, m).

PREPARATION 24

4'-Amino-3'-(2-fluorophenoxy)acetophenone was prepared according to a similar manner to that of Preparation 4.
mp: 90° to 92° C.
IR (Nujol): 3500, 3370, 1660, 1630, 1595, 1570, 1500 cm$^{-1}$.
NMR (CDCl$_3$, δ): 2.48 (3H, s), 4.4 (2H, broad s), 6.7-7.7 (7H, m).
MASS (m/e): 245 (M$^+$), 230 (base peak).

PREPARATION 25

3'-(4-Fluorophenoxy)-4'-nitroacetophenone was prepared according to a similar manner to that of Preparation 21.
mp: 68° to 72° C.
IR (Nujol): 1700, 1610, 1590, 1520, 1500 cm$^{-1}$.
NMR (CDCl$_3$, δ): 2.57 (3H, s), 6.9-8.1 (7H, m).

PREPARATION 26

4'-Amino-3'-(4-fluorophenoxy)acetophenone was prepared according to a similar manner to that of Preparation 4.
IR (Nujol): 3500, 3360, 3220, 1665, 1630, 1590, 1500 cm$^{-1}$.
NMR (CDCl$_3$, δ): 2.45 (3H, s), 4.4 (2H, broad s), 6.8-7.8 (7H, m).
mp: 74° to 79° C.

PREPARATION 27

3'-(2-Chlorophenoxy)-4'-nitroacetophenone was prepared according to a similar manner to that of Preparation 21.
mp: 68° to 69° C.
IR (Nujol): 1690, 1610, 1580, 1530 cm$^{-1}$.
NMR (CDCl$_3$, δ): 2.55 (3H, s), 7.0-8.2 (7H, m).

PREPARATION 28

4'-Amino-3'-(2-chlorophenoxy)acetophenone (oil) was prepared according to a similar manner to that of Preparation 4.
IR (Film): 3500, 3360, 1660, 1620, 1590, 1520 cm$^{-1}$.
NMR (CDCl$_3$, δ): 2.45 (3H, s), 4.4 (2H, broad s), 6.7-7.8 (7H, m).

PREPARATION 29

3'-(4-Chlorophenoxy)-4'-nitroacetophenone was prepared according to a similar manner to that of Preparation 21.
mp: 72° to 74° C.
IR (Nujol): 1695, 1610, 1585, 1525 cm$^{-1}$.
NMR (CDCl$_3$, δ): 2.58 (3H, s), 6.8-8.1 (7H, m).

PREPARATION 30

4'-Amino-3'-(4-chlorophenoxy)acetophenone (oil) was prepared according to a similar manner to that of Preparation 4.
IR (Film): 3500, 3380, 1665, 1620, 1590, 1515 cm$^{-1}$.
NMR (CDCl$_3$, δ): 2.45 (3H, s), 4.3 (2H, broad s), 6.7-7.9 (7H, m).

PREPARATION 31

3'-(2,4-Dichlorophenoxy)-4'-nitroacetophenone was prepared according to a similar manner to that of Preparation 21.
mp: 101° to 103° C.
IR (Nujol): 1700, 1610, 1520 cm$^{-1}$.
NMR (CDCl$_3$, δ): 2.58 (3H, s), 6.9-8.1 (6H, m).

PREPARATION 32

4'-Amino-3'-(2,4-dichlorophenoxy)acetophenone was prepared according to a similar manner to that of Preparation 4.
mp: 125° to 126° C.
IR (Nujol): 3500, 3370, 1660, 1630, 1595, 1570, 1520 cm$^{-1}$.
NMR (CDCl$_3$, δ): 2.47 (3H, s), 6.7-7.7 (6H, m).

PREPARATION 33

A solution of 3-(2,4-difluorophenoxy)-4-nitrobenzoyl chloride (2.2 g) in tetrahydrofuran (8 ml) was added dropwise to a stirred solution of dimethylamine (50% in water; 2 ml) in water (10 ml) at 5° C. The mixture was stirred for 30 minutes at 5° C. and for 1 hour at room temperature. The mixture was concentrated and extracted with chloroform. The extract was washed with water, dried, and concentrated under reduced pressure. The residue (2.4 g) was solidified with a mixture of hexane and ethanol to give pale brown powder of N,N-dimethyl-3-(2,4-difluorophenoxy)-4-nitrobenzamide (2.0 g).
mp: 81° to 83° C.
IR (Nujol): 1630, 1610, 1590, 1530, 1505 cm$^{-1}$.
NMR (CDCl$_3$, δ): 2.90 (3H, s), 3.03 (3H, s), 6.8-8.0 (6H, m).
MASS (m/e): 322 (M$^+$), 278 (base peak).

PREPARATION 34

4'-(2,4-Difluorophenoxy)-3'-nitroacetophenone was prepared according to a similar manner to that of preparation 21.
mp: 84° to 85° C.
IR (Nujol): 1695, 1620, 1575, 1540, 1505 cm$^{-1}$.
NMR (CDCl$_3$, δ): 2.60 (3H, s), 6.8-7.4 (4H, m), 8.10 (1H, dd, J=9, 2 Hz), 8.55 (1H, d, J=2 Hz).

PREPARATION 35

3'-Amino-4'-(2,4-difluorophenoxy)acetophenone was prepared according to a similar manner to that of Preparation 4.
mp: 108° to 109° C.
IR (Nujol): 3500, 3370, 1670, 1620, 1590, 1505 cm$^{-1}$.
NMR (CDCl$_3$, δ): 2.53 (3H, s), 4.1 (2H, broad s), 6.5-7.5 (6H, m).

PREPARATION 36

A solution of sodium nitrite (2 g) in water (3 ml) was added dropwise to a mixture of 5-chloro-2-methyl-4- nitroaniline (5 g) and concentrated hydrochloric acid (5.1 ml) in tetrahydrofuran (13 ml) and water (27 ml) at 5° C., and then the mixture was stirred for 1 hour. The resulting solution was added portionwise to a mixture of potassium cyanide (7.3 g) and cupric sulfate pentahydrate (9.7 g) in water (80 ml) at room temperature. The reaction mixture was stirred for 20 minutes, and extracted with ethyl acetate. The extract was washed with water, dried, and concentrated to give a solid (3.1 g). The solid was purified by column chromatography on silica gel (60 g) eluting with chloroform to give crystals of 5-chloro-2-methyl-4-nitrobenzonitrile.

IR (Nujol): 2240, 1565, 1530 cm$^{-1}$.

PREPARATION 37

5-(2,4-Difluorophenoxy)-2-methyl-4-nitrobenzonitrile was prepared according to a similar manner to that of Preparation 21.

mp: 95° to 97° C.
IR (Nujol): 2240, 1620, 1535, 1505 cm$^{-1}$.
NMR (CDCl$_3$, δ): 2.56 (3H, s), 6.8–7.3 (4H, m), 7.80 (1H, s).
MASS (m/e): 290 (M+).

PREPARATION 38

N,N-Dimethyl-4-amino-3-(2,4-difluorophenoxy)benzamide was prepared according to a similar manner to that of Preparation 4.

mp: 122° to 124° C.
IR (Nujol): 3500, 3320, 3210, 1635, 1615, 1575, 1500 cm$^{-1}$.

PREPARATION 39

2-(2,4-Difluorophenoxy)-4-trifluoromethylaniline was prepared according to a similar manner to that of Preparation 4.

IR (Film): 3520, 3430, 1630, 1505 cm$^{-1}$.

PREPARATION 40

4-Amino-5-(2,4-difluorophenoxy)-2-methylbenzonitrile was prepared according to a similar manner to that of Preparation 4.

IR (Nujol): 3520, 3380, 2220, 1630, 1500 cm$^{-1}$.

PREPARATION 41

A mixture of 3'-chloro-4'-nitroacetophenone (3 g), m-chlorophenol (2.3 g) and potassium carbonate (2.5 g) in xylene (30 ml) was stirred and refluxed for 7 hours. The insoluble was filtered and the filtrate was washed with an aqueous solution of sodium hydroxide (10%) and water, dried, and concentrated. The residue was purified by column chromatography on silica gel eluting with toluene to give an oil of 3'-(3-chlorophenoxy)-4'-nitroacetophenone (2.4 g).

IR (Film): 1695, 1585, 1530 cm$^{-1}$.
NMR (CDCl$_3$, δ): 2.58 (3H, s), 6.8–8.2 (7H, m).

PREPARATION 42

The following compound was obtained according to a similar manner to that of Preparation 41.

3'-(2,5-Dichlorophenoxy)-4'-nitroacetophenone.
mp: 90° to 94° C.
IR (Nujol): 1700, 1610, 1580, 1530 cm$^{-1}$.
NMR (CDCl$_3$, δ): 2.60 (3H, s), 7.0–8.2 (6H, m).

PREPARATION 43

A mixture of 3'-(3-chlorophenoxy)-4'-nitroacetophenone (2.4 g), iron powder (2.4 g) and ammonium chloride (0.24 g) in ethanol (32 ml) and water (16 ml) was refluxed with stirring for 1 hour. The insoluble was filtered and the filtrate was concentrated under reduced pressure. The residue was dissolved in ethyl acetate (30 ml), washed with water (20 ml), dried, and concentrated to give an oil of 4'-amino-3'-(3-chlorophenoxy)acetophenone (2.3 g).

IR (Film): 3500, 3370, 3220, 1660, 1620, 1580, 1520 cm$^{-1}$.
NMR (CDCl$_3$, δ): 2.50 (3H, s), 4.4 (2H, broad s), 6.7–7.9 (6H, m).

PREPARATION 44

The following compound was obtained according to a similar manner to that of Preparation 43.

4'-Amino-3'-(2,5-dichlorophenoxy)acetophenone, an oil.
IR (Nujol): 3500, 3360, 1660, 1620, 1590 cm$^{-1}$.
NMR (CDCl$_3$, δ): 2.49 (3H, s), 4.27 (2H, s), 6.7–7.8 (6H, m).

PREPARATION 45

A mixture of 2-(3-chloro-4-nitrophenyl)-2-methyl-1,3-dioxolane (4 g) and potassium 2,6-dichlorophenoxide (4 g) in N,N-dimethylformamide (40 ml) was stirred for 10 hours at 150° C. The reaction mixture was poured into water (200 ml) and extracted with ethyl acetate. The extract was washed with water, dried, and concentrated to give an oil (5.8 g). The oil was purified by column chromatography on silica gel (100 g) eluting with toluene to give prisms of 2-[3-(2,6-dichlorophenoxy)-4-nitrophenyl]-2-methyl-1,3-dioxolane (4.1 g).

mp: 90° to 92° C.
IR (Nujol): 1610, 1520, 1445 cm$^{-1}$.
NMR (CDCl$_3$, δ): 2.57 (3H, s), 3.5–4.3 (4H, m), 6.75 (1H, d, J=2 Hz), 7.1–8.2 (5H, m).

PREPARATION 46

A mixture of 2-[3-(2,6-dichlorophenoxy)-4-nitrophenyl]-2-methyl-1,3-dioxolane (3.9 g) and 3N hydrochloric acid (15 ml) in acetone (30 ml) was refluxed for 2.5 hours. The mixture was concentrated under reduced pressure. To the residue were added water (50 ml) and ethyl acetate (60 ml). The organic layer was dried and concentrated to give an amorphous powder of 3'-(2,6-dichlorophenoxy)-4'-nitroacetophenone (3.4 g).

mp: 131° to 133° C.
IR (Nujol): 1695, 1605, 1525 cm$^{-1}$.
NMR (CDCl$_3$, δ): 2.54 (3H, s), 7.1–8.1 (6H, m).

PREPARATION 47

The following compound was obtained according to a similar manner to that of Preparation 43.

4'-Amino-3'-(2,6-dichlorophenoxy)acetophenone.
mp: 153° to 155° C.
IR (Nujol): 3470, 3350, 1660, 1620, 1590 cm$^{-1}$.
NMR (CDCl$_3$, δ): 2.40 (3H, s), 4.0 (2H, broad s), 6.7–7.6 (6H, m).

PREPARATION 48

The following compound was obtained according to a similar manner to that of Preparation 41.

3'-(2-Bromophenoxy)-4'-nitroacetophenone, an oil.
IR (Film): 1695, 1610, 1580, 1530 cm$^{-1}$.
NMR (CDCl$_3$, δ): 2.57 (3H, s), 7.0–8.2 (7H, m).

PREPARATION 49

The following compound was prepared according to a similar manner to that of Preparation 43.

4'-Amino-3'-(2-bromophenoxy)acetophenone, an oil.
IR (Film): 3500, 3370, 1660, 1620, 1590 cm$^{-1}$.
NMR (CDCl$_3$, δ): 2.47 (3H, s), 4.4 (2H, broad s), 6.7-7.8 (7H, m).

PREPARATION 50

The following compound was obtained according to a similar manner to that of Preparation 41.

3'-(2-Methoxyphenoxy)-4'-nitroacetophenone.
mp: 94° to 96° C.
IR (Nujol): 1695, 1610, 1520, 1495 cm$^{-1}$.
NMR (CDCl$_3$, δ): 2.52 (3H, s), 3.77 (3H, s), 6.9-8.1 (7H, m).

PREPARATION 51

The following compound was obtained according to a similar manner to that of Preparation 43.

4'-Amino-3'-(2-methoxyphenoxy)acetophenone.
mp: 126° to 127° C.
IR (Nujol): 3500, 3360 1655, 1615, 1570, 1500 cm$^{-1}$.
NMR (CDCl$_3$, δ): 2.40 (3H, s), 3.85 (3H, s), 4.23 (2H, s), 6.7-7.7 (7H, m).

PREPARATION 52

The following compound was prepared according to a similar manner to that of Preparation 41.

3'-(2-Chloro-4-fluorophenoxy)-4'-nitroacetophenone, an oil.
IR (Film): 1695, 1605, 1530, 1480 cm$^{-1}$.
NMR (CDCl$_3$, δ): 2.58 (3H, s), 6.9-8.2 (6H, m)

PREPARATION 53

The following compound was obtained according to a similar manner to that of Preparation 43.

4'-Amino-3'-(2-chloro-4-fluorophenoxy)acetophenone.
mp: 117° to 119° C.
IR (Nujol): 3490, 3350, 1650, 1620, 1590, 1565 cm$^{-1}$.

PREPARATION 54

The following compound was obtained according to a similar manner to that of Preparation 41.

3-(2,4-Dichlorophenoxy)-4-nitrobenzonitrile.
mp: 113° to 116° C.
IR (Nujol): 2250, 1610, 1590, 1580, 1520 cm$^{-1}$.
NMR (CDCl$_3$, δ): 7.0-7.7 (5H, m), 8.05 (1H, d, J=8 Hz).

PREPARATION 55

The following compound was prepared according to a similar manner to that of Preparation 43.

4-Amino-3-(2,4-dichlorophenoxy)benzonitrile.
mp: 125° to 126° C.
IR (Nujol): 3500, 3390, 2210, 1630, 1600, 1520 cm$^{-1}$.
NMR (CDCl$_3$, δ): 4.5 (2H, broad s), 6.8-7.7 (6H, m).

PREPARATION 56

The following compound was obtained according to a similar manner to that of Preparation 4.

1-[4-Amino-3-(2,4-difluorophenoxy)benzoyl]-4-methylpiperazine, an oil.
IR (Film): 3500, 3350, 3220, 1620, 1500 cm$^{-1}$.

PREPARATION 57

The following compound was obtained according to a similar manner to that of Preparation 4.

4'-Amino-5'-(2,4-difluorophenoxy)-2'-methylacetophenone
mp: 95° to 99° C.
IR (Nujol): 3480, 3380, 1650, 1620, 1560, 1505 cm$^{-1}$.

PREPARATION 58

The following compound was obtained according to a similar manner to that of Preparation 4.

2-(2,4-Difluorophenoxy)-4-(methylthio)aniline, an oil.

PREPARATION 59

The following compound was obtained according to a similar manner to that of Preparation 4.

N-Methoxy-4-amino-3-(2,4-difluorophenoxy)benzamide, an oil.
IR (Film): 3500, 3350, 3200, 1660, 1620, 1570, 1500 cm$^{-1}$.
NMR (CDCl$_3$, δ): 3.74 (3H, s), 3.9 (2H, broad s), 6.6-7.4 (6H, m), 8.9 (1H, broad s).

PREPARATION 60

A mixture of 3-(2,4-difluorophenoxy)-4-nitrobenzoic acid (2.1 g) and phosphorus pentachloride (1.6 g) in benzene (20 ml) was stirred for 2 hours at room temperature. The mixture was concentrated under reduced pressure to give crystals of 3-(2,4-difluorophenoxy)-4-nitrobenzoyl chloride (2.2 g). A solution of 3-(2,4-difluorophenoxy)-4-nitrobenzoyl chloride (2.2 g) in benzene (20 ml) was added to a mixture of aluminum chloride (2.4 g) in benzene (20 ml). The mixture was stirred overnight at ambient temperature and concentrated under reduced pressure. The residue was dissolved in chloroform, washed with diluted hydrochloric acid and water successively, dried over magnesium sulfate, and concentrated under reduced pressure. The residue was recrystallized from a mixture of hexane and ethanol to give crystals of 3-(2,4-difluorophenoxy)-4-nitrobenzophenone (2.3 g).
mp: 72° to 73° C.
IR (Nujol): 1660, 1610, 1600, 1525, 1510 cm$^{-1}$.
NMR (CDCl$_3$, δ): 6.7-8.1 (11H, m)
MASS (m/e): 355 (M+).

PREPARATION 61

The following compound was obtained according to similar manner to that of Preparation 4.

4 Amino-3 (2,4-difluorophenoxy)benzophenone.
mp: 110° to 113° C.
IR (Nujol): 3520, 3370, 1625, 1595, 1565, 1505 cm$^{-1}$.

PREPARATION 62

The following compound was obtained according to a similar manner to that of Preparation 3.

3'-(2,3-Dichlorophenoxy)-4'-nitroacetophenone.
mp: 74° to 78° C.
IR (Nujol): 1690, 1605, 1570, 1520 cm$^{-1}$.
NMR (CDCl$_3$, δ): 2.58 (3H, s), 6.9-8.2 (6H, m).

PREPARATION 63

The following compound was obtained according to a similar manner to that of Preparation 4.

4'-Amino-3'-(2,3-dichlorophenoxy)acetophenone.
mp: 102° to 106° C.

IR (Nujol): 3500, 3370, 1660, 1620, 1590 cm$^{-1}$.
NMR (CDCl$_3$, δ): 2.47 (3H, s), 4.35 (2H, s), 6.7–8.0 (6H, m).

PREPARATION 64

The following compound was prepared according to a similar manner to that of Preparation 45.

2-Methyl-2-[4-nitro-3-(2,4,6-trichlorophenoxy)-phenyl]-1,3-dioxolane.

mp: 121° to 125° C.
IR (Nujol): 1600, 1520, 1450 cm$^{-1}$.
NMR (CDCl$_3$, δ): 1.56 (3H, s), 3.5–4.2 (4H, m), 6.6–8.1 (5H, m).

PREPARATION 65

A mixture of 2-methyl-2-[4-nitro-3-(2,4,6-trichlorophenoxy)phenyl]-1,3-dioxolane (1.7 g) and 3N-hydrochloric acid (5 ml) in acetone (15 ml) was refluxed for 2 hours. The mixture was concentrated under reduced pressure. To the residue were added water and ethyl acetate. The organic layer was dried and concentrated to give a powder of 4'-nitro-3'-(2,4,6-trichlorophenoxy)acetophenone (1.5 g).

mp: 135° to 138° C.
IR (Nujol): 1695, 1600, 1540 cm$^{-1}$.
NMR (CDCl$_3$, δ): 2.60 3H, s), 7.2–8.2 (5H, m).

PREPARATION 66

The following compound was obtained according to a similar manner to that of Preparation 4.

4'-Amino-3'-(2,4,6-trichlcrophenoxy)acetophenone.

mp: 183° to 186° C.
IR (Nujol): 3490, 3360, 1660, 1625, 1445 cm$^{-1}$.
NMR (CDCl$_3$, δ): 2.43 (3H, s), 4.1 (2H, broad s), 6.7–7.6 (5H, m).

PREPARATION 67

The following compound was obtained according to a similar manner to that of Preparation 3.

3'-(2-Methylthiophenyl)-4'-nitroacetophenone.

mp: 84° to 86° C.
IR (Nujol): 1690, 1605, 1590, 1520 cm$^{-1}$.
NMR (CDCl$_3$, δ): 2.43 (3H, s), 2.52 (3H, s), 6.9–8.3 (7H, m).

PREPARATION 68

The following compound was obtained according to a similar manner to that of Preparation 4.

4'-Amino-3'-(2-methylthiophenoxy)acetophenone, an oil.

IR (Film): 3480, 3360, 1660, 1620, 1590, 1515 cm$^{-1}$.
NMR (CDCl$_3$, δ): 2.50 (6H, s), 4.20 (2H, s), 6.7–7.9 (7H, m).

PREPARATION 69

The following compound was obtained according to a similar manner to that of Preparation 3.

3'-(2-Methylphenoxy)-4'-nitroacetophenone, an oil.

IR (Film): 1695, 1605, 1580, 1530 cm$^{-1}$.
NMR (CDCl$_3$, δ): 2.25 3H, s), 2.52 (3H, s), 6.8–8.2 (7H, m).

PREPARATION 70

The following compound was prepared according to a similar manner to that of Preparation 4.

4'-Amino-3'-(2-methylphenoxy)acetophenone, an oil.
IR (Film): 3500, 3370, 1660, 1620, 1590, 1520 cm$^{-1}$.

NMR (CDCl$_3$, δ): 2.30 (3H, s), 2.44 (3H, s), 4.15 (2H, broad s), 6.6–7.7 (7H, m).

Preparation 71

A mixture of 3-(2,4-difluorophenoxy)-4-nitrobenzoic acid (1.5 g) and phosphorus pentachloride (1.1 g) in benzene (10 ml) was stirred for 1 hour at room temperature. The mixture was concentrated under reduced pressure to give crystals of 3-(2,4-difluorophenoxy)-4-nitrobenzoyl chloride. A solution of the above chloride in dichloromethane (5 ml) was added to a mixture of methoxylamine hydrochloride (0.85 g) and sodium bicarbonate (2.2 g) in water (10 ml) and dichloromethane (5 ml) at to 5° C. After stirring for 1 hour at the same temperature, the mixture was extracted with ethyl acetate. The extract was washed with water, dried, and concentrated. The residue was crystallized from isopropyl ether to give pale brown crystals of N-methoxy-3-(2,4-difluorophenoxy)-4-nitrobenzamide (1.2 g).

mp: 103° to 105° C.
IR (Nujol): 3250, 1660, 1615, 1590, 1530, 1505 cm$^{-1}$.
NMR (CDCl$_3$, δ): 3.76 (3H, s), 6.8–8.0 (6H, m), 9.49 (1H, s).

PREPARATION 72

The following compound was obtained according to a similar manner to that of Preparation 71.

1-[3-(2,4-Difluorophenoxy)-4-nitrobenzoyl]-4-methylpiperazine.

mp: 75° to 78° C.
IR (Nujol): 1635, 1610, 1525, 1505 cm$^{-1}$.
NMR (CDCl$_3$, δ): 2.30 (3H, s), 2.2–2.6 (4H, m), 3.2–3.9 (4H, m), 6.8–7.5 (5H, m), 8.07 (1H, d, J=8 Hz).
MASS (m/e): 377 (M+).

PREPARATION 73

A mixture of 4'-amino-3'-(2,4-difluorophenoxy)acetophenone (1.7 g), pyridine (0.52 g), and iodobenzene dichloride (1.8 g) in tetrahydrofuran (20 ml) was stirred overnight at 5° C. The mixture was concentrated. The residue was dissolved in ethyl acetate and washed with water, an aqueous solution of sodium bisulfite, and water. The organic layer was evaporated to give a powder of 4'-amino-3'-chloro-5'-(2,4-difluorophenoxy)acetophenone (1.5 g).

mp: 142° to 144° C.
IR (Nujol): 3500, 3400, 1670, 1610, 1565, 1505 cm$^{-1}$.
NMR (CDCl$_3$, δ): 2.43 (3H, s), 4.85 (2H, broad s), 6.7–7.3 (4H, m), 7.65 (1H, d, J=2 Hz).
MASS (m/e): 297 (M+), 282.

PREPARATION 74

A mixture of 5-(2,4-difluorophenoxy)-2-methyl-4-nitrobenzonitrile (1.5 g), concentrated sulfuric acid (2 ml) and water (2 ml) was stirred for 3 hours at 150° C. The mixture was dissolved in a mixture of ethyl acetate and water. The insoluble was filtered off. The organic layer was separated, washed with water, dried over magnesium sulfate, and concentrated to give a powder of 5-(2,4-difluorophenoxy)-2-methyl-4-nitrobenzoic acid (1.4 g).

IR (Nujol): 3100, 1715, 1620, 1525, 1510 cm$^{-1}$.

PREPARATION 75

A mixture of 5-(2,4-difluorophenoxy)-2-methyl-4-nitrobenzoic acid (1.4 g) and phosphorus pentachloride (1 g) in benzene (10 ml) was stirred for 1 hour at room temperature. The mixture was concentrated under reduced pressure to give an oil of 5-(2,4-difluorophenoxy)-2-methyl-4-nitrobenzoyl chloride (1.6 g). A solution of diethyl malonate (0.88 g) and ethanol (0.5 ml) in ether (5 ml) was added dropwise to a stirred solution of magnesium (132 mg), ethanol (0.2 ml), and carbon tetrachloride (0.3 ml) in ether (5 ml) at room temperature. The mixture was stirred for 1 hour at room temperature and refluxed for 30 minutes. To the resulting mixture was added dropwise a solution of 5-(2,4-difluorophenoxy)-2-methyl-4-nitrobenzoyl chloride (1.6 g) in ether (3 ml) at 5° C. The mixture was stirred for 2 hours at room temperature and refluxed for 1 hour. The reaction mixture was poured into 10% sulfuric acid (40 ml) and extracted with ethyl acetate. The extract was washed with water, dried, and concentrated to give an oil of diethyl 5-(2,4-difluorophenoxy)-2-methyl-4-nitrobenzoylmalonate (2.1 g).

IR (Film): 1750, 1730, 1620, 1580, 1530, 1505 cm$^{-1}$.

A mixture of diethyl 5-(2,4-difluorophenoxy)-2-methyl-4-nitrobenzoylmalonate (2.1 g) and sulfuric acid (1 ml) in acetic acid (6 ml) and water (5 ml) was refluxed for hours. The reaction mixture was neutralized with an aqueous solution of sodium hydroxide, and extracted with ethyl acetate. The extract was washed with water, dried and concentrated. The oily residue was purified by column chromatography on silica gel (25 g) eluting with a mixture of toluene and ethyl acetate (10:1) to give crystals of 5'-(2,4-difluorophenoxy)-2'-methyl-4'-nitroacetophenone (0.69 g).

mp: 110° to 113° C.

IR (Nujol): 1710, 1620, 1580, 1520, 1500 cm$^{-1}$.

NMR (CDCl$_3$, δ): 2.46 (3H, s), 2.49 (3H, s), 6.8-7.3 (4H, m), 7.78 (1H, s).

MASS (m/e): 307 (M+).

PREPARATION 76

A solution of sodium nitrite (2.03 g) in water (4 ml) was added dropwise to a stirred mixture of 3-(2,4-difluorophenoxy)-4-nitroaniline (7 g) and concentrated hydrochloric acid (7.6 ml) in water (16 ml) and ethanol (16 ml) at 5° to 7° C. The mixture was stirred for 20 minutes at the same temperature. The resulting mixture was added portionwise to a stirred solution of potassium O-ethyl dithiocarbonate (5.9 g) in water (60 ml) at 65° C. After stirring for 20 minutes at 65° C., the mixture was extracted with toluene. The extract was washed with water, dried over magnesium sulfate, and concentrated to give an oil (8.6 g).

The oil was stirred with a mixture of sodium borohydride (0.7 g) and potassium hydroxide (1.8 g) in methanol (50 ml) for 15 minutes at 5° to 10° C. The reaction mixture was acidified with 10% sulfuric acid and concentrated. The residue was dissolved in ethyl acetate, washed with water, dried and evaporated to dryness. The residue was crystallized from a mixture of ethanol and hexane to give crystals of 3-(2,4-difluorophenoxy)-4-nitrothiophenol (4.1 g).

IR (Nujol): 2570, 1610, 1595, 1575, 1510 cm$^{-1}$.

PREPARATION 77

Methyl iodide (2 g) was added to a stirred solution of 3-(2,4-difluorophenoxy)-4-nitrothiophenol (2 g) and potassium hydroxide (0.51 g) in methanol (10 ml) and water (10 ml). The mixture was stirred for 20 minutes. The precipitates were filtered, washed with 50% methanol, and dried to give 2',4'-difluoro-5-methylthio-2-nitrodiphenyl ether (2 g).

mp: 56° to 61° C.

IR (Nujol): 1610, 1580, 1510 cm$^{-1}$.

PREPARATION 78

A mixture of 3-(2,4-difluorophenoxy)-4-nitrobenzoyl chloride (2.1 g) and potassium thiocyanate (2.8 g) in toluene (20 ml) was refluxed overnight. Ethyl mercaptan (2.6 ml) was added to the resulting mixture. The mixture was stirred for 4 hours at 60° C. and concentrated. The residue was dissolved in ethyl acetate and washed with water. The organic layer was dried over magnesium sulfate and concentrated to give crystals of ethyl N-[3-(2,4-difluorophenoxy)-4-nitrobenzoyl]dithiocarbamate (2.2 g).

mp: 136° to 138° C.

IR (Nujol) 1700, 1610, 1590, 1500 cm$^{-1}$.

NMR (DMSO-d6, δ): 1.30 (3H, t, J=7 Hz), 3.24 (2H, q, J=7 Hz), 7.2-8.4 (6H, m), 12.75 (1H, broad s).

MASS (m/e): 336, 278.

PREPARATION 79

A solution of ethyl iodide (0.349 ml) in tetrahydrofuran (6.5 ml) was added dropwise to a stirred mixture of ethyl N-[3-(2,4-difluorophenoxy)-4-nitrobenzoyl]dithiocarbamate (1.5 g) and potassium hydroxide (285 mg) in tetrahydrofuran (33 ml). The mixture was stirred overnight at room temperature and concentrated under reduced pressure. The residue was dissolved in chloroform, washed with water, dried over magnesium sulfate, and concentrated to give a yellow oil of diethyl [3-(2,4-difluorophenoxy)-4-nitrobenzoylimino]dithiocarbonate (1.7 g).

IR (Film): 1640, 1605, 1590, 1530, 1500 cm$^{-1}$.

PREPARATION 80

Hydroxylamine hydrochloride (324 mg) and diethyl [3-(2,4-difluorophenoxy)-4-nitrobenzoylimino]dithiocarbonate (1.6 g) were added to a solution of sodium (102 mg) in methanol (20 ml). The mixture was refluxed for 5 hours and concentrated. The residue was dissolved in chloroform, washed with water, dried over magnesium sulfate, and concentrated to give a yellow powder of 5-[3-(2,4-difluorophenoxy)-4-nitrophenyl]-3-ethylthio-1,2,4-oxadiazole (1.2 g).

mp: 103° to 105° C.

IR (Nujol): 1620, 1565, 1500 cm$^{-1}$.

NMR (DMSO-d$_6$, δ): 1.40 (3H, t, J=7 Hz), 3.24 (2H, q, J=7 Hz), 7.1-8.5 (6H, m).

MASS (m/e): 379 (M+), 278.

PREPARATION 81

A mixture of 5-[3-(2,4-difluorophenoxy)-4-nitrophenyl]-3-ethylthio-1,2,4-oxadiazole (1.18 g), iron powder (1.2 g), and ammonium chloride (0.12 g) in ethanol (20 ml) and water (10 ml) was refluxed with stirring for 50 minutes. The insoluble material was filtered, and the filtrate was concentrated to dryness. The residue was dissolved in ethyl acetate, washed with water, dried and concentrated. The residue (1.1 g) was purified by column chromatography on silica gel (26 g) eluting with a mixture of toluene and ethyl acetate (20:1) to give a pale yellow powder of S-ethyl 4-amino-3-(2,4-difluorophenoxy)benzoyliminothiocarbamate (0.68 g).

IR (Nujol): 3500, 3400, 3310, 3150, 1610, 1550, 1500 cm$^{-1}$.

NMR (DMSO-d$_6$, δ): 1.18 (3H, t, J=7 Hz), 2.95 (2H, q, J=7 Hz), 5.8 (2H, s), 6.7-7.8 (6H, m), 9.15 (2H, broad s).

MASS (m/e): 351 (M+), 279, 248.

EXAMPLE 1

A mixture of 4'-amino-3'-(2,4-difluorophenoxy)acetophenone (2.2 g) and methanesulfonyl chloride (0.96 g) in pyridine (10 ml) was stirred overnight at room temperature. Pyridine was evaporated under reduced pressure, and the resulting oil was triturated with diluted hydrochloric acid to give crystals (2.8 g). The crystals were recrystallized from ethanol to give pale yellow crystals of 4'-acetyl-2'-(2,4-difluorophenoxy)methanesulfonanilide (2.3 g).

mp: 117° to 118° C.
IR (Nujol): 3220, 1685, 1605, 1590, 1505, 1345 cm$^{-1}$.
NMR (CDCl3 $\delta$): 2.50 (3H. s), 3.11 (3H, s), 6.7–7.8 (7H, m).
MASS (m/e): 341 (M+), 326, 262.

The following compounds were prepared according to a similar manner to that of Example 1.

EXAMPLE 2

4'-Propionyl-2'-(2,4-difluorophenoxy)methanesulfonanilide.
mp: 107° to 109° C.
IR (Nujol): 3240, 1675, 1610, 1505, 1445, 1350 cm$^{-1}$.
NMR (CDCl$_3$, $\delta$): 1.17 (3H, t, J=7 Hz), 2.89 (2H, q, J=7 Hz), 3.12 (3H, s), 6.8–7.8 (7H, m).
MASS (m/e): 355 (M+), 326 (base peak).

EXAMPLE 3

4'-Cyano-2'-(2,4-difluorophenoxy)methanesulfonanilide.
mp: 185° to 187° C.
IR (Nujol): 3330, 2250, 1610, 1585, 1510 cm$^{-1}$.
NMR (CDCl$_3$+CD$_3$OD, $\delta$): 3.14 (3H, s), 6.9–7.8 (6H, m).

EXAMPLE 4

A mixture of 4-amino-3-(2,4-difluorophenoxy)benzamide (0.82 g) and methanesulfonyl chloride (0.39 g) in pyridine (5 ml) was stirred for 15 minutes at 5° C. and for 30 minutes at room temperature. Pyridine was evaporated under reduced pressure, and the residue was dissolved in ethyl acetate, washed with diluted hydrochloric acid and a saturated aqueous solution of sodium chloride, dried over magnesium sulfate, and concentrated under reduced pressure. The residue (1.1 g) was subjected to column chromatography on silica gel (20 g) eluting with a mixture of toluene and ethyl acetate (1:2). The fractions containing the desired compound were combined and concentrated to give colorless crystals of 3-(2,4-difluorophenoxy)-4-(methanesulfonamido)benzamide (0.74 g).

mp: 147° to 150° C.
IR (Nujol): 3460, 3280, 3170, 1680, 1615, 1585, 1505 cm$^{-1}$.
NMR (CDCl$_3$, $\delta$): 3.10 (3H, s), 5.94 (2H, broad s), 6.8–7.9 (7H, m).
MASS (m/e): 342 (M+, base peak).

EXAMPLE 5

A mixture of N-methyl-4-amino-3-(2,4-difluorophenoxy)benzamide (0.77 g) and methanesulfonyl chloride (314 mg) in pyridine (5 ml) was stirred for 30 minutes at 5° C. and for an hour at room temperature. Pyridine was evaporated under reduced pressure, and the residue was dissolved in ethyl acetate, washed with diluted hydrochloric acid and a saturated aqueous solution of sodium chloride successively, dried over magnesium sulfate, and concentrated to give a syrup (1 g). The syrup was crystallized from a mixture of ethyl acetate and hexane to give colorless needles of N-methyl-3-(2,4-difluorophenoxy)-4-(methanesulfonamido)benzamide (0.79 g).

mp: 137° to 139° C.
IR (Nujol): 3460, 3270, 1650, 1615, 1550, 1505 cm$^{-1}$.
NMR (CDCl$_3$, $\delta$): 2.92 (3H, d, J=5 Hz), 3.06 (3H, s), 6.05 (1H, broad s), 6.7–7.7 (7H, m).
MASS (m/e): 356 (M+, base peak), 326, 277.

EXAMPLE 6

Ethyl 3-(2,4-difluorophenoxy)-4-(methanesulfonamido)benzoate was prepared according to a similar manner to that of Example 5.

mp: 111° to 113° C.
IR (Nujol): 3250, 1715, 1610, 1590, 1505 cm$^{-1}$.
NMR (CDCl$_3$, $\delta$): 1.33 (3H, t, J=7 Hz), 3.10 (3H, s), 4.32 (2H, q, J=7 Hz), 6.7–8.0 (7H, m).
MASS (m/e): 371 (M+), 326, 292 (base peak).

EXAMPLE 7

A mixture of 4'-acetyl-2'-(2,4-difluorophenoxy)methanesulfonanilide (1.5 g), hydroxylamine hydrochloride (0.31 g) and pyridine (0.35 g) in ethanol (20 ml) was refluxed for 1 hour. The reaction mixture was concentrated under reduced pressure, and the residue was triturated with water to give white powder (1.54 g). The powder was recrystallized from a mixture of ethanol and water to give pale yellow needles of 2'-(2,4-difluorophenoxy)-4'-[1-(hydroxyimino)ethyl]methanesulfonanilide (1.4 g).

mp: 150° to 151° C.
IR (Nujol): 3300, 1610, 1580, 1510 cm$^{-1}$.
NMR (CDCl$_3$+CD$_3$OD, $\delta$): 2.17 (3H, s), 3.07 (3H, s), 6.7–7.7 (6H, m).
MASS (m/e): 356 (M+), 277 (base).

EXAMPLE 8

A mixture of 4'-cyano-2'-(2,4-difluorophenoxy)methanesulfonanilide (1.3 g) and concentrated hydrochloric acid (13 ml) in acetic acid (8 ml) was refluxed for 8 hours. The precipitates were filtered, washed with water, dried, and recrystallized from a mixture of ethyl acetate and hexane to give crystals of 3-(2,4-difluorophenoxy)-4-(methanesulfonamido)benzoic acid (0.72 g).

mp: 167° to 169° C.
IR (Nujol): 3300, 1710, 1615, 1510 cm$^{-1}$.
NMR (CDCl$_3$+CD$_3$OD; $\delta$): 3.17 (3H, s), 6.9–8.0 (6H, m).
MASS (m/e): 343 (M+), 264 (base).

EXAMPLE 9

A mixture of 4'-amino-3'-phenoxyacetophenone (0.96 g) and methanesulfonyl chloride (0.58 g) in pyridine (10 ml) was stirred for 3 hours at room temperature. The mixture was poured into ice-water and extracted with ethyl acetate. The extract was washed with 2N-hydrochloric acid, dried over magnesium sulfate, and concentrated under reduced pressure. The residue (1.4 g) was subjected to column chromatography on silica gel (40 g) eluting with a mixture of toluene and ethyl acetate (20:1). The fractions containing the desired compound were combined and concentrated under reduced pressure to give crystals (1.15 g). The crystals were recrystallized from a mixture of ethanol and water (1:1) to give needles of 4'-acetyl-2'-phenoxymethanesulfonanilide (0.98 g).

mp: 113° to 114° C.
IR (Nujol): 3250, 1690, 1610, 1505 cm$^{-1}$.
NMR (CDCl$_3$, δ): 2.49 (3H, s), 3.07 (3H, s), 6.9–7.8 (9H, m).
MASS (m/e): 305 (M+, 226 (base peak).

EXAMPLE 10

4'-Acetyl-2'-(2-fluorophenoxy)methanesulfonanilide was prepared according to a similar manner to that of Example 9.
mp: 92°–94° C.
IR (Nujol): 3220, 1680, 1600, 1585, 1520, 1500 cm$^{-1}$.
NMR (CDCl$_3$, δ): 2.50 (3H, s), 3.11 (3H, s), 7.1–7.8 (8H, m).
MASS (m/e): 323 (M+), 308, 244.

EXAMPLE 11

4'-Acetyl-2'-(4-fluorophenoxy)methanesulfonanilide was prepared according to a similar manner to that of Example 9.
mp: 95°–96° C.
IR (Nujol): 3250, 1680, 1605, 1500 cm$^{-1}$.
NMR (CDCl$_3$, δ): 2.49 (3H, s), 3.10 (3H, s), 6.9–7.7 (8H, m).
MASS (m/e): 323 (M+), 244.

EXAMPLE 12

4'-Acetyl-2'-(2-chlorophenoxy)methanesulfonanilide was prepared according to a similar manner to that of Example 9.
mp: 102° to 103° C.
IR (Nujol): 3350, 1675, 1605, 1580, 1500 cm$^{-1}$.
NMR (CDCl$_3$, δ): 2.50 (3H, s), 3.12 (3H, s), 7.0–7.9 (8H, m).
MASS (m/e): 339 (M+), 324, 225 (base peak).

EXAMPLE 13

4'-Acetyl-2'-(4-chlorophenoxy)methanesulfonanilide was prepared according to a similar manner to that of Example 9.
mp: 103° to 104° C.
IR (Nujol): 3150, 1675, 1605, 1575, 1510, 1485 cm$^{-1}$.
NMR (CDCl$_3$, δ): 2.50 (3H, s), 3.08 (3H, s), 6.9–7.8 (8H, m).
MASS (m/e): 339 (M+), 324, 225 (base peak).

EXAMPLE 14

4'-Acetyl-2'-(2,4-dichlorophenoxy)methanesulfonanilide was prepared according to a similar manner to that of Example 9.
mp: 119° to 121° C.
IR (Nujol): 3300, 1680, 1610, 1580, 1500 cm$^{-1}$.
NMR (CDCl$_3$, δ): 2.50 (3H, s), 3.11 (3H, s), 7.0–7.8 (7H, m).
MASS (m/e): 373 (M+, 358, 259 (base peak).

EXAMPLE 15

N,N-Dimethyl-3-(2,4-difluorophenoxy)-4-(methanesulfonamido)benzamide was prepared according to a similar manner to that of Example 9.
mp: 165° to 167° C.
IR (Nujol): 3100, 1630, 1580, 1505, 1490 cm$^{-1}$.
NMR (CDCl$_3$, δ): 3.00 (3H, s), 3.12 (3H, s), 6.7–7.8 (7H, m).
MASS (m/e): 370 (M+), 326 (base peak).

EXAMPLE 16

A mixture of 4'-acetyl-2'-(2,4-difluorophenoxy)methanesulfonanilide (1.3 g), methoxylamine hydrochloride (0.32 g), and pyridine (0.31 g) in ethanol (20 ml) was refluxed with stirring for 1 hour. The mixture was concentrated under reduced pressure, and the residue was triturated with water to give crystals (1.4 g). The crystals were recrystallized from ethanol to give 2'-(2,4-difluorophenoxy)-4'-[1-(methoxyimino)ethyl]methanesulfonanilide (1.2 g).
mp: 118° to 120° C.
IR (Nujol): 3300, 1615, 1510 cm$^{-1}$.
NMR (CDCl$_3$, δ): 2.12 (3H, s), 3.07 (3H, s), 3.93 (3H, s), 6.8–7.8 (7H, m).
MASS (m/e): 370 (M+, 291 (base peak).

EXAMPLE 17

4'-Acetyl-2'-(2,4-difluorophenoxy)ethanesulfonanilide was prepared according to a similar manner to that of Example 9.
mp: 103° to 105° C.
IR (Nujol): 3200, 1680, 1605, 1585, 1500 cm$^{-1}$.
NMR (CDCl$_3$, δ): 1.40 (3H, t, J=7.5 Hz), 2.49 (3H, s), 3.24 (2H, q, J=7.5 Hz), 6.8–7.9 (7H, m).
MASS (m/e): 355 (M+), 262.

EXAMPLE 18

A mixture of 4'-amino-3'-(2,4-difluorophenoxy)acetophenone (2.0 g) and dimethylsulfamoyl chloride (11 g) in pyridine (20 ml) was stirred for 11 hours at 80° C. After cooling, the reaction mixture was poured into 2N aqueous solution of hydrochloric acid (200 ml) and extracted with ethyl acetate. The extract was washed with water, dried, and concentrated in vacuo. The residue was purified by column chromatography on silica gel (100 g) eluting with a mixture of toluene and ethyl acetate (20:1), and recrystallized from a mixture of ethanol and water (2:1, 15 ml) to give prisms of 3'-(2,4-difluorophenoxy)-4'-(dimethylsulfamoylamino)acetophenone (0.94 g).
mp: 80° to 82° C.
IR (Nujol): 3280, 1680, 1610, 1510 cm$^{-1}$.
NMR (CDCl$_3$, δ): 2.50 (3H, s), 2.91 (6H, s), 6.8–7.7 (7H, m).
MASS (m/e): 370 (M+), 262.

EXAMPLE 19

5'-Acetyl-2'-(2,4-difluorophenoxy)methanesulfonanilide was prepared according to a similar manner to that of Example 1.
mp: 142° to 143° C.
IR (Nujol): 3240, 1680, 1610, 1590, 1500 cm$^{-1}$.
NMR (CDCl$_3$, δ): 2.56 (3H, s), 3.10 (3H, s), 6.72 (1H, d, J=9 Hz), 6.9–7.4 (4H, m), 7.73 (1H, dd, J=9, 2 Hz), 8.30 (1H, d, J=2 Hz).
MASS (m/e): 341 (M+), 326, 262.

EXAMPLE 20

4'-Cyano-2'-(2,4-difluorophenoxy)-5'-methylmethanesulfonanilide was prepared according to a similar manner to that of Example 1.
mp: 193° to 194° C.
IR (Nujol): 3250, 2230, 1615, 1580, 1505 cm$^{-1}$.
NMR (CDCl$_3$, δ): 2.53 (3H, s), 3.16 (3H, s), 6.8–7.7 (6H, m).
MASS (m/e): 338 (M+), 259 (base peak).

EXAMPLE 21

The following compound was obtained according to a similar manner to that of Example 1.

4'-Acetyl-2'-(2,5-dichlorophenoxy)methanesulfonanilide, pale yellow needles.
mp: 175° to 177° C.
IR (Nujol): 3230, 1670, 1605, 1580, 1500 cm$^{-1}$.
NMR (CDCl$_3$, $\delta$): 2.52 (3H, s), 3.12 (3H, s), 7.0-7.8 (7H, m).

EXAMPLE 22

The following compound was obtained according to a similar manner to that of Example 1.

4'-Acetyl-2'-(2,6-dichlorophenoxy)methanesulfonanilide.
mp: 155° to 156° C.
IR (Nujol): 3220, 1675, 1605, 1500 cm$^{-1}$.
NMR (CDCl$_3$, $\delta$): 2.49 (3H, s), 3.12 (3H, s), 7.0-7.9 (7H, m).
MASS (m/e): 373 (M+), 259.

EXAMPLE 23

The following compound was obtained according to a similar manner to that of Example 1.

4'-Acetyl-2'-(2-bromophenoxy)methanesulfonanilide.
mp: 95° to 96° C.
IR (Nujol): 3200, 1670, 1610, 1580, 1500 cm$^{-1}$.
NMR (CDCl$_3$, $\delta$): 2.50 (3H, s), 3.12 (3H, s), 7.0-7.9 (8H, m).
MASS (m/e): 383 (M+), 225.

EXAMPLE 24

The following compound was obtained according to a similar manner to that of Example 1.

4'-Acetyl-2'-(2-methoxyphenoxy)methanesulfonanilide.
mp: 160° to 161° C.
IR (Nujol): 3280, 1675, 1605, 1500 cm$^{-1}$.
NMR (CDCl$_3$, $\delta$): 2.48 (3H, s), 3.02 (3H, s), 3.78 (3H, s), 6.8-7.8 (7H, m).
MASS (m/e): 335 (M+), 225.

EXAMPLE 25

The following compound was obtained according to a similar manner to that of Example 1.

4'-Acetyl-2'-(2-chloro-4-fluorophenoxy)methanesulfonanilide.
mp: 96° to 98° C.
IR (Nujol): 3230, 1680, 1605, 1580, 1515 cm$^{-1}$.
NMR (CDCl$_3$, $\delta$): 2.50 (3H, s), 3.13 (3H, s), 7.0-7.8 (7H, m).
MASS (m/e): 357 (M+), 342, 243.

EXAMPLE 26

The following compound was obtained according to a similar manner to that of Example 1.

4'-Cyano-2'-(2,4-dichlorophenoxy)methanesulfonanilide.
mp: 164° to 165° C.
IR (Nujol): 3320, 2230, 1610, 1510 cm$^{-1}$.
NMR (CDCl$_3$, $\delta$): 3.14 (3H, s), 6.8-7.9 (7H, m).
MASS (m/e): 356 (M+), 242.

EXAMPLE 27

A mixture of 4-amino-3-(2,4-difluorophenoxy)benzophenone (2.1 g) and methanesulfonyl chloride (0.77 g) in pyridine (10 ml) was stirred overnight at room temperature. Pyridine was evaporated under reduced pressure, and the residue was dissolved in ethyl acetate, washed with diluted hydrochloric acid and water successively, dried, and concentrated under reduced pressure. The residue (2 g) was dissolved in methanol (20 ml) and treated with sodium hydroxide (0.2 g). The mixture was concentrated under reduced pressure and the residue was solidified from ethanol to give pale yellow powder of 2'-(2,4-difluorophenoxy)-4'-benzoylmethanesulfonanilide sodium salt (1.5 g).
mp: 160° to 170° C. (dec.).
IR (Nujol): 3450 (broad), 1640, 1590, 1500 cm$^{-1}$.
NMR (D$_2$O, $\delta$): 2.94 (3H, s), 6.6-7.4 (11H, m).

EXAMPLE 28

A mixture of 4'-cyano-2'-(2,4-difluorophenoxy)methanesulfonanilide (1.5 g) and Raney's Nickel (1.5 g) in 75% formic acid (40 ml) was refluxed for 2 hours. The mixture was filtered and the filtrate was concentrated to dryness. The residue was recrystallized from ethanol to give pale yellow needles of 2'-(2,4-difluorophenoxy)-4'-formylmethanesulfonanilide (1.4 g).
mp: 156° to 157° C.
IR (Nujol): 3300, 1690, 1605, 1505 cm$^{-1}$.
NMR (CDCl$_3$, $\delta$): 3.17 (3H, s), 6.7-7.9 (7H, m), 9.84 (1H, s).
MASS (m/e): 327 (M+), 248.

EXAMPLE 29

A mixture of 4'-acetyl-2'-(2,4-difluorophenoxy)methanesulfonanilide (1.5 g) and tert-butyl aminooxyacetate (0.71 g) in ethanol (5 ml) was refluxed for 13 hours. The mixture was concentrated and the residue was dissolved in ethyl acetate, washed with water, dried over magnesium sulfate, and concentrated under reduced pressure. The residual oil was suspended in ether and the insoluble material was filtered off. The filtrate was concentrated to give an oil of 4'-[1-(tertbutyloxycarbonylmethoxyimino)ethyl]-2'-(2,4-difluorophenoxy)methanesulfonanilide (2.6 g).
IR (Film): 3250, 1745, 1615, 1580, 1510 cm$^{-1}$.
NMR (CDCl$_3$, $\delta$): 1.44 (9H, s), 2.20 (3H, s), 3.05 (3H, s), 4.53 (2H, s), 6.8-7.7 (7H, m).

EXAMPLE 30

A solution of 4'-[1-(tert-butyloxycarbonylmethoxyimino)ethyl]-2'-(2,4-difluorophenoxy)methanesulfonanilide (2.6 g), anisole (2 ml), and trifluoroacetic acid (6 ml) in dichloromethane (50 ml) was stirred for 5 hours at room temperature. The mixture was concentrated, and the residue was dissolved in an aqueous solution of sodium bicarbonate and washed with ethyl acetate. The aqueous layer was acidified with hydrochloric acid and extracted with ethyl acetate. The extract was washed with water, dried, and concentrated under reduced pressure. The residue was recrystallized from a mixture of hexane and ethyl acetate to give pale yellow powder of 4'-[1-(carboxymethoxyimino)ethyl]-2'-(2,4-difluorophenoxy)methanesulfonanilide (1.5 g).
mp: 174° to 175° C.
IR (Nujol): 3370, 1730, 1705, 1620, 1505 cm$^{-1}$.
NMR (CDCl$_3$+CD$_3$OD, $\delta$): 2.22 (3H, s), 3.06 (3H, s), 4.67 (2H, s), 6.8-7.7 (6H, m).
MASS (m/e): 414 (M+).

EXAMPLE 31

A mixture of 2'-(2,4-difluorophenoxy)-4'-formylmethanesulfonanilide (2.3 g) and triphenylphosphoranylideneacetone (2.3 g) in dimethylsulfoxide (10 ml) was stirred for 13 hours at 80° C. After cooling of the mixture, ethyl acetate was added, and the resulting mixture was washed with water, then dried. The ethyl acetate layer was evaporated to dryness and the residue was purified by column chromatography on silica gel (80 g) eluting with a mixture of chloroform and methanol (200:1) and further recrystallized from ethanol to give pale yellow needles of 2'-(2,4-difluorophenoxy)-4'-(3-oxo-1-butenyl)methanesulfonanilide (1.0 g).

mp: 130° to 132° C.
IR (Nujol): 3230, 1645, 1575, 1510 cm$^{-1}$.
NMR (CDCl$_3$, δ): 2.33 (3H, s), 3.10 (3H, s), 6.50 (1H, d, J=16 Hz), 6.8–7.8 (8H, m).
MASS (m/e): 367 (M+), 288 (base peak).

EXAMPLE 32

Sodium borohydride (0.18 g) was added portionwise to a solution of 4'-acetyl-2'-(2,4-difluorophenoxy)methanesulfonanilide (1.34 g) in methanol (25 ml) at room temperature. The mixture was stirred for 30 minutes, treated with acetic acid (1 ml), and concentrated under reduced pressure. The residue was dissolved in ethyl acetate, washed with an aqueous solution of sodium bicarbonate, and dried over magnesium sulfate. The ethyl acetate layer was evaporated to dryness and the residue was recrystallized from a mixture of ethanol and water to give pale yellow prisms of 2'-(2,4-difluorophenoxy)-4'-(1-hydroxyethyl)methanesulfonanilide (0.97 g).

mp: 103° to 105° C.
IR (Nujol): 3480, 1615, 1585, 1500 cm$^{-1}$.
NMR (CDCl$_3$, δ): 1.37 (3H, d, J=6 Hz), 2.10 (1H, d, J=4 Hz), 3.00 (3H, s), 4.6–4.9 (1H, m), 6.7–7.7 (7H, m).
MASS (m/e): 343 (M+), 328, 222.

EXAMPLE 33

The following compound was obtained according to a similar manner to that of Example 1.

4'-Acetyl-2'-(3-chlorophenoxy)methanesulfonanilide, an oil.

The above oil (2.4 g) was solidified in an aqueous solution of sodium hydroxide (10%, 20 ml) to give a powder of 4'-acetyl-2'-(3-chlorophenoxy)methanesulfonanilide sodium salt (2.3 g).

mp: 290° to 300° C. (dec.).
IR (Nujol): 1660, 1590, 1550 cm$^{-1}$.
NMR (DMSO-d$_6$, δ): 2.34 (3H, s), 2.52 (3H, s), 6.7–7.8 (7H, m).

EXAMPLE 34

The following compound was obtained according to a similar manner to that of Examples 1 and 33.

4'-Acetyl-2'-(2,3-dichlorophenoxy)methanesulfonanilide sodium salt.

mp: 162° to 170° C. (dec.).
IR (Nujol): 1665, 1590, 1550, 1500 cm$^{-1}$.
NMR (DMSO-d$_6$, δ): 2.40 (3H, s), 2.55 (3H, s), 6.55 (1H, dd, J=6, 5 Hz), 7.1–7.8 (5H, m).

EXAMPLE 35

The following compound was obtained according to a similar manner to that of Example 1.

4'-Acetyl-2'-(2,4,6-trichlorophenoxy)methanesulfonanilide.

mp: 199° to 201° C.
IR (Nujol): 3370, 1680, 1610, 1510 cm$^{-1}$.

NMR (CDCl$_3$, δ): 2.50 (3H, s), 3.12 (3H, s), 7.0–7.9 (4H, m), 7.43 (2H, s).
MASS (m/e): 407 (M+), 392, 293.

EXAMPLE 36

The following compound was obtained according to a similar manner to that of Example 1.

4'-Acetyl-2'-(2-methylthiophenoxy)methanesulfonanilide.

mp: 122° to 125° C.
IR (Nujol): 3280, 1670, 1600, 1500 cm$^{-1}$.
NMR (CDCl$_3$, δ): 2.43 (3H, s), 2.50 (3H, s), 3.02 (3H, s), 6.9–7.8 (8H, m).
MASS (m/e): 351 (M+), 225, 148.

EXAMPLE 37

A solution of m-chloroperbenzoic acid (80%; 0.77 g) in dichloromethane (12 ml) was added dropwise to a stirred solution of 4'-acetyl-2'-(2-methylthiophenoxy)methanesulfonanilide (1.2 g) in dichloromethane (12 ml) at 5° C. The solution was stirred for 1 hour at 5° to 10° C., washed with a saturated aqueous solution of sodium bicarbonate (15 ml), dried over magnesium sulfate, and concentrated. The oily residue (1.4 g) was crystallized from ethanol to give crystals of 4'-acetyl-2'-(2-methylsulfinylphenoxy)methanesulfonanilide (0.77 g).

mp: 113° to 116° C.,
IR (Nujol): 1690, 1610, 1580, 1505 cm$^{-1}$.
NMR (CDCl$_3$, δ): 2.57 (3H, s), 2.98 (3H, s), 3.00 (3H, s), 6.8–7.9 (7H, m), 8.98 (1H, s).
MASS (m/e): 367 (M+), 270, 225.

EXAMPLE 38

To a stirred solution of 4'-acetyl-2'-(2-methylthiophenoxy)methanesulfonanilide (1.2 g) in acetic acid (7 ml) was added dropwise 30% hydrogen peroxide (1 ml). The mixture was stirred for 2 hours at 70° C. and cooled to room temperature. Ethanol (10 ml) was added, and the precipitates were filtered and washed with ethanol to give colorless needles of 4'-acetyl-2'-(2-methylsulfonylphenoxy)methanesulfonanilide (1.1 g).

mp: 189° to 191° C.
IR (Nujol): 3290, 1680, 1610, 1580, 1510 cm$^{-1}$.
NMR (DMSO-d$_6$, δ); 2.50 (3H, s), 3.15 (3H, s), 3.43 (3H, s), 7.0–8.1 (7H, m), 9.9 (1H, s).
MASS (m/e): 383 (M+), 225.

EXAMPLE 39

The following compound was obtained according to a similar manner to that of Examples 1 and 33.

4'-Acetyl-2'-(2-methylphenoxy)methanesulfonanilide sodium salt.

mp: 150° to 160° C. (dec.)
IR (Nujol): 3450, 1650, 1590, 1550, 1495 cm$^{-1}$.
NMR (D$_2$O, δ): 2.20 (3H, s), 2.38 (3H, s), 3.00 (3H, s), 6.8–7.8 (7H, m).

EXAMPLE 40

A mixture of 4'-acetyl-2'-(2,4-difluorophenoxy)methanesulfonanilide (1.5 g), semicarbazide hydrochloride (0.5 g), and pyridine (0.35 g) in ethanol (20 ml) was stirred and refluxed for 2 hours. The mixture was concentrated under reduced pressure. The residue was triturated with water, filtered, and recrystallized from methanol to give a powder of 3'-(2,4-difluorophenoxy)-4'-methanesulfonamidoacetophenone semicarbazone (1.1 g).

mp: 187° to 189° C.

IR (Nujol): 3500, 3200, 1710, 1580, 1505 cm$^{-1}$.
NMR (DMSO-d$_6$, δ): 2.10 (3H, s), 3.04 (3H, s), 6.33 (2H, s), 6.9–7.7 (6H, m), 9.26 (1H, s), 9.43 (1H, s).
MASS (m/e): 398 (M+).

EXAMPLE 41

The following compound was obtained according to a similar manner to that of Example 40.
3'-(2,4-Difluorophenoxy)-4'-methanesulfonamidoacetophenone thiosemicarbazone.
mp: 219° to 220° C. (dec.).
IR (Nujol): 3480, 3360, 3200, 1590, 1500 cm$^{-1}$.
NMR (DMSO-d$_6$, δ): 2.22 (3H, s), 3.07 (3H, s), 7.0–8.4 (8H, m), 9.57 (1H, s), 10.20 (1H, s).
MASS (m/e): 414 (M+), 398, 339.

EXAMPLE 42

The following compound was obtained in a similar manner to that of Example 40.
2'-(2,4-Difluorophenoxy)-4'-(hydroxyiminomethyl)-methanesulfonanilide.
mp: 155° to 157° C.
IR (Nujol): 3300, 1610, 1505 cm$^{-1}$.
NMR (CDCl$_3$, δ): 3.10 (3H, s), 5.7 (1H, broad s), 6.8–7.8 (7H, m), 8.00 (1H, s).
MASS (m/e): 342 (M+), 263.

EXAMPLE 43

The following compound was obtained according to a similar manner to that of Example 40.
2'-(2,4-Difluorophenoxy)-4'-(methoxyiminomethyl)-methanesulfonanilide.
mp: 110° to 112° C.
IR (Nujol): 3400, 1620, 1510 cm$^{-1}$.
NMR (CDCl$_3$, δ): 3.07 (3H, s), 3.93 (3H, s), 6.8–7.8 (7H, m), 7.93 (1H, s).
MASS (m/e): 356 (M+), 277.

EXAMPLE 44

The following compound was obtained in a similar manner to that of Example 40.
2'-(2,4-Difluorophenoxy)-4'-(1-ethoxyiminoethyl)methanesulfonanilide.
mp: 114° to 116° C.
IR (Nujol): 3250, 1610, 1505 cm$^{-1}$.
NMR (CDCl$_3$, δ): 1.24 (3H, t, J=7 Hz), 2.11 (3H, s), 3.03 (3H, s), 4.17 2H, q, J=7 Hz), 6.8–7.8 (7H, m).
MASS (m/e): 384 (M+), 305.

EXAMPLE 45

A mixture of 4'-cyano-2'-(2,4-difluorophenoxy)methanesulfonanilide (1.5 g), hydroxylamine hydrochloride (0.8 g), and sodium carbonate (1.2 g) in ethanol (21 ml) and water (32 ml) was refluxed for 13 hours. The mixture was concentrated and the residue was dissolved in water, acidified with diluted hydrochloric acid, and extracted with ethyl acetate. The extract was washed with water, dried, and concentrated. The residue was purified by column chromatography on silica gel (40 g) eluting with a mixture of toluene and ethyl acetate (1:1) to give colorless crystals of 3-(2,4-difluorophenoxy)-4-(methanesulfonamido)benzamidoxime (1.0 g).
mp: 174° to 175° C.
IR (Nujol): 3500, 3425, 3300, 1650, 1610, 1590, 1510 cm$^{-1}$.
NMR (CDCl$_3$-CD$_3$OD, δ): 3.07 (3H, s), 6.8–7.8 (6H, m).
MASS (m/e): 357 (M+), 278.

EXAMPLE 46

The following compound was obtained according to a similar manner to that of Example 1.
N-Methoxy-3-(2,4-difluorophenoxy)-4-(methanesulfonamido)benzamide.
mp: 125° to 127° C.
IR (Nujol): 3150, 1635, 1580, 1500 cm$^{-1}$.
NMR (CDCl$_3$, δ): 3.12 (3H, s), 3.84 (3H, s), 6.8–7.8 (8H, m).
MASS (m/e): 372 (M+), 342, 326.

EXAMPLE 47

The following compound was obtained according to a similar manner to that of Example 1.
1-[3-(2,4-Difluorophenoxy)-4-(methanesulfonamido)-benzoyl]-4-methylpiperazine.
mp: 159° to 160° C.
IR (Nujol): 1625, 1575, 1500 cm$^{-1}$.
NMR (CDCl$_3$-CD$_3$OD, δ): 2.35 (3H, s), 2.3–2.6 (4H, m), 3.10 (3H, s), 3.4–3.8 (4H, m), 6.7–7.8 (6H, m).
MASS (m/e): 425 (M+).

EXAMPLE 48

A mixture of 2'-(2,4-difluorophenoxy)-4'-formylethanesulfonanilide (2 g) and α-triphenylphosphoranylidene-γ-butyrolactone (2.2 g) in dimethyl sulfoxide (10 ml) was stirred at 80° C. for 6 hours. The mixture was dissolved in ethyl acetate, and the resulting mixture was washed with water, dried, and concentrated to dryness. The residue was purified by column chromatography on acetate (1:1) to give a powder of α-[3-(2,4-difluorophenoxy)-4-(methanesulfonamido)benzylidene]-γ-butyrolactone (1.7 g).
mp: 179° to 180° C.
IR (Nujol): 3260, 1740, 1645, 1605, 1505 cm$^{-1}$.
NMR (acetone-d$_6$, δ): 3.0–3.4 (2H, m), 3.20 (3H, s), 4.43 (2H, t, J=7 Hz), 7.1–7.9 (7H, m), 8.6 (1H, broad s).
MASS (m/e): 395 (M+), 316.

EXAMPLE 49

A solution of bromine (479 mg) in chloroform (2.5 ml) was added dropwise to a stirred solution of 4'-acetyl-2'-(2,4-difluorophenoxy)methanesulfonanilide (1 g) and benzoyl peroxide (4.3 mg) in chloroform (15 ml. After stirring for 1 hour at room temperature, the mixture was washed with water, then with a diluted aqueous solution of sodium bisulfite and again with water. The chloroform solution was dried and concentrated under reduced pressure to give 4'-bromoacetyl-2'-(2,4-difluorophenoxy)methanesulfonanilide.

A mixture of the above obtained compound, and thiourea (334 mg) in methanol (10 ml) was refluxed for 1 hour. The mixture was evaporated to dryness and the residue was triturated with an aqueous solution of sodium bicarbonate to give a powder (1.3 g). The powder was purified by column chromatography on silica gel (20 g) eluting with a mixture of chloroform and methanol (20:1), and recrystallized from ethanol to give crystals of 4'-(2-amino-4-thiazolyl)-2'-(2,4-difluorophenoxy)methanesulfonanilide (0.74 g).
mp: 182° to 183° C.
IR (Nujol): 3480, 3340, 3130, 1620, 1540, 1500 cm$^{-1}$.
NMR (CD$_3$OD, δ): 3.07 (3H, s), 6.77 (1H, s), 7.0–7.6 (6H, m).
MASS (m/e): 397 (M+), 318.

EXAMPLE 50

A solution of 4'-(2-amino-4-thiazolyl)-2'-(2,4-difluorophenoxy)methanesulfonanilide (1.2 g) in acetic anhydride (3 ml) was stirred for 30 minutes at 80° C. The mixture was concentrated, and then evaporated with xylene and ethanol. The residue (1.4 g) was purified by column chromatography on silica gel (30 g) eluting with a mixture of toluene and ethyl acetate (1:1), and recrystallized from ethanol to afford pale brown crystals of 4'-(2-acetamido-4-thiazolyl)-2'-(2,4-difluorophenoxy)methanesulfonanilide (0.82 g).

mp: 192° to 193° C.
IR (Nujol): 3200, 1660, 1550, 1500 cm$^{-1}$.
NMR (CDCl$_3$, δ): 2.00 (3H, s), 3.07 (3H, s), 6.7–7.8 (8H m), 10.1 (1H, broad s).
MASS (m/e): 439 (M+), 360.

EXAMPLE 51

A solution of 4'-bromoacetyl-2'-(2,4-difluorophenoxy)methanesulfonanilide (2.5 g) and pyridine (526 mg) in dichloromethane (20 ml) was refluxed for 4 hours. The mixture was concentrated, and the residue was dissolved in water and washed with ethyl acetate. To the aqueous layer was added sodium bicarbonate, giving an amorphous powder. The powder 0.76 g was dissolved in an ethanolic solution of hydrogen chloride. The residue obtained by evaporation of the solution was crystallized with ethyl acetate to give a powder of 1-[3-(2,4-difluorophenoxy)-4-(methanesulfonamido)benzoylmethyl]pyridinium chloride (0.75 g).

mp: 203° to 205° C. (dec.).
IR (Nujol): 3400, 1700, 1635, 1610, 1500 cm$^{-1}$.
NMR (CD$_3$OD, δ): 3.20 (3H, s), 6.40 (2H, s), 7.0–9.0 (11H, m).
MASS (m/e): 419, 341.

EXAMPLE 52

A mixture of 4'-amino-3-'chloro-5'-(2,4-difluorophenoxy)acetophenone (2.4 g) and methanesulfonic anhydride (2.5 g) was stirred at 100° C. for 1 hour. The mixture was concentrated to dryness. The residue was dissolved in chloroform, washed with a saturated aqueous solution of sodium bicarbonate, dried, and concentrated to give an oil (2.5 g). The oil was purified by column chromatography on silica gel (50 g) eluting with chloroform. The purified product (oil) was dissolved in a solution of sodium hydroxide (180 mg) in methanol (20 ml), and the solution was evaporated. The residual oil was crystallized from ethyl acetate, affording a powder of 4'-acetyl-2'-chloro-6'-(2,4-difluorophenoxy)methanesulfonanilide sodium salt (1.1 g).

mp: 270° to 272° C.
IR (Nujol): 1665, 1585, 1545, 1505 cm$^{-1}$.
NMR (CD$_3$OD, δ): 2.43 (3H, s), 2.92 (3H, s), 6.7–7.3 (4H, m), 7.77 (1H, d, J=2 Hz).

EXAMPLE 53

The following compound was obtained according to a similar manner to that of Example 1.

4'-Acetyl-2'-(2,4-difluorophenoxy)-5'-methylmethanesulfonanilide.

mp: 116° to 117° C.
IR (Nujol): 3260, 1680, 1670, 1610, 1575, 1505 cm$^{-1}$.
NMR (CDCl$_3$, δ): 2.40 (3H, s), 2.51 (3H, s),
Mass (m/e): 355 (M+), 340, 276.

EXAMPLE 54

The following compound was prepared in a similar manner to that of Example 40.

5'-(2,4-Difluorophenoxy)-4'-methanesulfonamido-2'-methylacetophenone semicarbazone.

mp: 216° to 217° C.
IR (Nujol): 3500, 3250, 1710, 1615, 1590, 1510 cm$^{-1}$.
NMR (DMSO-d$_6$, δ): 2.05 (3H, s), 2.30 (3H, s), 3.05 (3H, s), 6.23 (2H, s), 6.76 (1H, s), 7.0–7.7 (4H, m), 9.21 (1H, s), 9.38 (1H, s).
MASS (m/e): 412 (M+), 397, 369, 354.

EXAMPLE 55

A solution of sodium nitrite (1.56 g) in water (3 ml) was added dropwise to a stirred mixture of 4'-amino-2'-(2,4-difluorophenoxy)methanesulfonanilide (6.2 g) and concentrated hydrochloric acid (5.8 ml) in water (50 ml) at 5° to 10° C., and the mixture was stirred for 15 minutes at the same temperature. The resulting mixture was added dropwise to a stirred solution of potassium O-ethyl dithiocarbonate (10 g) in water (40 ml) at 65° C. After stirring for 15 minutes at 65° C., the mixture was extracted with toluene. The extract was washed with water, dried over magnesium sulfate, and concentrated to give an oil (10 g).

The oil was stirred with a mixture of sodium borohydride (0.54 g) and potassium hydroxide (3 g) in methanol (100 ml) for 1 hour at room temperature. The reaction mixture was acidified with 10% sulfuric acid and concentrated. The residue was dissolved in ethyl acetate, washed with water, dried, and evaporated to dryness. The residue (7 g) was purified by column chromatography on silica gel (150 g) eluting with chloroform and recrystallized from a mixture of ethyl acetate and hexane to give crystals of 2'-(2,4-difluorophenoxy)-4'-mercaptomethanesulfonanilide (4.4 g).

mp: 103° to 105° C.
IR (Nujol): 3280, 2600, 1620, 1580, 1500 cm$^{-1}$.
NMR (CDCl$_3$, δ): 3.00 (3H, s), 6.54 (1H, s), 6.6–7.5 (7H, m).
MASS (m/e): 331 (M+), 252.

EXAMPLE 56

The following compound was obtained according to a similar manner to that of Example 1.

2'-(2,4-Difluorophenoxy)-4'-(methylthio)methanesulfonanilide.

mp: 76° to 78° C.
IR (Nujol): 3300, 1610, 1580, 1500 cm$^{-1}$.
NMR (CDCl$_3$, δ): 2.35 (3H, s), 3.00 (3H, s), 6.4–7.6 (7H, m).

EXAMPLE 57

The following compound was prepared in a similar manner to that of Example 37.

2'-(2,4-Difluorophenoxy)-4'-(methylsulfinyl)methanesulfonanilide mp: 164° to 166° C.
IR (Nujol): 1615, 1500 cm$^{-1}$.
NMR (CDCl$_3$-CD$_3$OD, δ): 2.70 (3H, s), 3.10 (3H, s), 6.8–7.9 (6H, m).

EXAMPLE 58

A mixture of 2'-(2,4-difluorophenoxy)-4'-(methylthio)methanesulfonanilide (0.45 g) and m-chloroperbenzoic acid (80%; 0.62 g) in dichloromethane (10 ml) was stirred at room temperature for 1 hour. The mixture was washed with a saturated aqueous solution of sodium bicarbonate and water, dried, and concentrated. The residue was recrystallized from ethanol to give crystals of 2'-(2,4-difluorophenoxy)-4'-(methylsulfonyl)methanesulfonanilide.

mp: 182° to 184° C.

IR (Nujol): 3260, 1620, 1595, 1505 cm$^{-1}$.

NMR (CDCl$_3$-CD$_3$OD, δ): 3.00 (3H, s), 3.13 (3H, s), 6.8–8.0 (6H, m).

EXAMPLE 59

A mixture of 2'-(2,4-difluorophenoxy)-4'-mercaptomethanesulfonanilide (1.5 g), p-chloronitrobenzene (0.75 g) and potassium carbonate (0.66 g) in xylene (30 ml) was stirred and refluxed for 5 hours. The reaction mixture was acidified, washed with water, dried, and concentrated to dryness. The residual oil was crystallized from ethanol to give crystals of 2'-(2,4-difluorophenoxy)-4'-(4-nitrophenylthio)methanesulfonanilide (1.5 g).

mp: 124° to 127° C.

IR (Nujol): 3250, 1615, 1580, 1500 cm$^{-1}$.

NMR (CDCl$_3$, δ): 3.10 (3H, s), 6.7–8.1 (11H, m).

EXAMPLE 60

A mixture of 2'-(2,4-difluorophenoxy)-4'-(4-nitrophenylthio)methanesulfonanilide (9.2 g), iron powder (9 g), and ammonium chloride (0.9 g) in ethanol (150 ml) and water (70 ml) was refluxed with stirring for 30 minutes. The insoluble was filtered and the filtrate was concentrated. The residue was dissolved in ethyl acetate, washed with water, dried, and concentrated to afford an oil (9 g). Concentrated hydrochloric acid (5 ml) was added to a solution of the above oil (5 g) in methanol (50 ml) to give crystals of 4'-(4-aminophenylthio)-2'-(2,4-difluorophenoxy)methanesulfonanilide hydrochloride (4.6 g).

mp: 218° to 221° C.

IR (Nujol): 3270, 2600, 1610, 1500 cm$^{-1}$.

NMR (DMSO-d$_6$, δ): 3.10 (3H, s), 6.6–7.6 (10H, m), 7.95 (3H, broad s), 9.51 (1H, s).

EXAMPLE 61

A mixture of 4'-cyano-2'-(2,4-difluorophenoxy)methanesulfonanilide (2.1 g), sodium azide (0.5 g) and ammonium chloride (0.43 g) in N,N-dimethylformamide (10 ml) was stirred for 6 hours at 110° C. The mixture was poured into a mixture of ice and diluted hydrochloric acid, and extracted with ethyl acetate. The extract was washed with water, dried and concentrated in vacuo. The residual crystals were recrystallized from ethyl acetate to give colorless crystals of 2'-(2,4-difluorophenoxy)-4'-(5-tetrazolyl)methanesulfonanilide (2.3 g).

mp: 222° to 223° C. (dec.)

IR (Nujol): 3250, 1620, 1590, 1505 cm$^{-1}$.

NMR (CDCl$_3$-CD$_3$OD, δ): 3.14 (3H, s), 6.8–7.8 (6H, m).

MASS (m/e): 367 (M+), 339.

EXAMPLE 62

A mixture of S-ethyl [4-amino-3-(2,4-difluorophenoxy)benzoylimino]thiocarbamate (0.64 g) and methanesulfonyl chloride (0.156 ml) in pyridine (4 ml) was stirred for 2 hours at room temperature. The reaction mixture was concentrated, and the residue was dissolved in ethyl acetate and washed with diluted hydrochloric acid and water successively. The organic layer was dried over magnesium sulfate and concentrated. The residue was purified by column chromatography on cilica gel eluting with a mixture of toluene and ethyl acetate (10:1) and recrystallization from ethanol to give crystals of S-ethyl [3-(2,4-difluorophenoxy)-4-methanesulfonamido)benzoylimino]thiocarbamate (0.6 g).

mp: 95° to 97° C.

IR (Film): 3400, 3250, 1610, 1570, 1500 cm$^{-1}$.

NMR (CDCl$_3$, δ): 1.30 (3H, t, J=7 Hz), 3.07 (2H, q, J=7 Hz), 3.13 (3H, s), 6.8–8.2 (9H, m).

MASS (m/e): 429 (M+), 326.

EXAMPLE 63

A mixture of 3-(2,4-difluorophenoxy)-4-methanesulfonamidobenzoic acid (0.6 g) and phosphorus pentachloride (0.4 g) in benzene (6 ml) was warmed, dissolved, and then stirred for 25 minutes at room temperature. The mixture was concentrated under reduced pressure to give a powder of 3-(2,4-difluorophenoxy)-4-methanesulfonamidobenzoyl chloride (0.7 g).

IR (Film): 3390, 3310, 1745, 1605, 1500 cm$^{-1}$.

EXAMPLE 64

A mixture of 3-(2,4-difluorophenoxy)-4-methanesulfonamidobenzoyl chloride (0.7 g) and potassium thiocyanate (0.73 g) in toluene (6 ml) was refluxed overnight. Ethyl mercaptan (0.68 ml) was added to the resulting mixture. The mixture was stirred for 5 hours at 60° C. and concentrated. The residue was dissolved in ethyl acetate and washed with water. The organic layer was dried and concentrated to give a yellow powder of ethyl N-[3-(2,4-difluorophenoxy)-4-methanesulfonamidobenzoyl]dithiocarbamate (0.83 g).

IR (Nujol): 3260, 1695, 1610, 1585, 1500 cm$^{-1}$.

NMR (DMSO-d$_6$, δ): 1.28 (3H, t, J=7 Hz), 3.17 (3H, s), 3.20 (2H, q, J=7 Hz), 7.2–8.0 (6H, m), 9.90 (1H, s), 12.4 (1H, broad s).

MASS (m/e): 326 (base).

EXAMPLE 65

A solution of ethyl iodide (1.4 ml) in tetrahydrofuran (27 ml) was added dropwise to a stirred mixture of ethyl N-[3-(2,4-difluorophenoxy)-4-methanesulfonamidobenzoyl]dithiocarbamate (6.8 g) and potassium hydroxide (1.15 g) in tetrahydrofuran (134 ml). The mixture was stirred overnight at room temperature and concentrated under reduced pressure. The residue was dissolved in chloroform, washed with water, dried and concentrated to give pale brown crystals of diethyl [3-(2,4-difluorophenoxy)-4-(methanesulfonamido)benzoylimino]dithiocarbonate (6.9 g).

NMR (DMSO-d$_6$, δ): 1.22 (6H, t, J=7 Hz), 3.09 (4H, q, J=7 Hz), 3.19 (3H, s), 7.1–7.9 (6H, m), 9.9 (1H, s).

EXAMPLE 66

Hydroxylamine hydrochloride (1.27 g) and diethyl [3-(2,4-difluorophenoxy)-4-(methanesulfonamido)benzoylimino]dithiocarbonate (6.9 g) were added to a solution of sodium (0.4 g) in methanol (100 ml). The mixture was refluxed overnight and concentrated. The residue was dissolved in chloroform, washed with water, dried and concentrated. The residual powder was purified by column chromatography on silica gel (75 g) eluting with a mixture of toluene and ethyl acetate (20:1) to give pale brown crystals of 5-[3-(2,4-difluorophenoxy)-4-methanesulfonamidophenyl]-3-ethylthio-1,2,4-oxadiazole.

mp: 116° to 119° C.

IR (Nujol): 3400, 1620, 1560, 1500 cm$^{-1}$.

NMR (DMSO-d$_6$, δ): 1.38 (3H, t, J=7 Hz), 3.20 (2H, q, J=7 Hz), 3.23 (3H, s), 7.2–7.9 (6H, m), 10.04 (1H, s).

MASS (m/e): 427 (M+), 326.

EXAMPLE 67

The following compound was obtained according to a similar manner to that of Example 58.

5-[3-(2,4-Difluorophenoxy)-4-methanesulfonamidophenyl]-3-ethylsulfonyl-1,2,4-oxadiazole.

mp: 168° to 169° C.

IR (Nujol): 3310, 1615, 1565, 1510 cm$^{-1}$.

NMR (DMSO-d$_6$, δ): 1.30 (3H, t, J=7Hz), 3.30 (3H, s), 3.68 (2H, q, J=7Hz), 7.2–8.0 (6H, m), 10.15 (1H, s).

MASS (m/e): 459 (M+), 367, 326.

EXAMPLE 68

A mixture of 4'-bromoacetyl-2'-(2,4-difluorophenoxy)methanesulfonanilide (2 g) and 20% aqueous solution of methanethiol sodium salt (5 ml) in chloroform (30 ml) was stirred for 2 hours at room temperature. The mixture was acidified with 10% hydrochloric acid. The organic layer was separated, washed with water, dried and evaporated to dryness. The oily residue (3.9 g) was purified by column chromatography on silica gel (80 g) eluting with a mixture of toluene and ethyl acetate (5:1), and then recrystallized from ethanol to give crystals of 2'-(2,4-difluorophenoxy)-4'-(methylthioacetyl)methanesulfonanilide (1.6 g), mp 74° to 76° C.

IR (Nujol): 3300, 1665, 1605, 1585, 1505 cm$^{-1}$.

NMR (CDCl$_3$, δ): 2.10 (3H, s), 3.17 (3H, s), 3.67 (2H, s), 6.8–7.8 (7H, m).

Mass (m/e): 387 (M+), 326.

EXAMPLE 69

A mixture of 2'-(2,4-difluorophenoxy)-4'-(methylthioacetyl)methanesulfonanilide (1.4 g) and m-chloroperbenzoic acid (1.4 g) in dichloromethane (15 ml) was stirred for 1 hour at room temperature. The mixture was washed with an aqueous solution of sodium bicarbonate and water, dried, and concentrated. The residue was recrystallized from ethyl acetate to give colorless crystals of 2'-(2,4-difluorophenoxy)-4'-(methylsulfonylacetyl)methanesulfonanilide (0.66 g), mp 162° to 163° C.

IR (Nujol): 3400, 1670, 1610, 1505 cm$^{-1}$.

NMR (DMSO-d$_6$, δ): 3.13 (3H, s), 3.23 (3H, s), 5.03 (2H, s), 7.1–8.1 (6H, m), 10.02 (1H, s).

MASS (m/e): 419 (M+), 340.

The following compounds were prepared in a similar manner to that of Example 1.

4'-Cyano-2'-(2,4-difluorophenoxy)-5'-chloromethanesulfonanilide mp: 232° to 233 ° C.

IR (Nujol): 3240, 2240, 1605, 1575, 1510, 1490 cm$^{-1}$.

NMR (DMSO-d$_6$, δ): 3.22 (3H, s), 6.9–7.6 (5H, m), 7.72 (1H, s).

MASS (m/e): 358 (M+), 279.

EXAMPLE 71

5'-Acetyl-4'-cyano-2'-(2,4-difluorophenoxy)methanesulfonanilide mp: 174° to 176 ° C.

IR (Nujol): 3400, 2230, 1690, 1605, 1575, 1510 cm$^{-1}$.

NMR (DMSO-d$_6$, δ): 2.61 (3H, s), 3.22 (3H, s), 7.0–7.7 (5H, m), 8.14 (1H, s).

MASS (m/e): 366(M+), 351.

EXAMPLE 72

2'-(2,4-Difluorophenoxy)-4'-pyruvoylmethanesulfonanilide mp: 109° to 111° C.

IR (Nujol) 3300, 3250, 1710, 1675, 1605, 1500 cm$^{-1}$.

NMR (CDCl$_3$): 2.46 (3H, s), 3.14 (3H, s), 6.8–7.8 (7H, m).

EXAMPLE 73

4'-Cyano-2'-(2,4-difluorophenoxy)methanesulfonanilide (15 g) was dissolved in a solution of sodium hydroxide (2 g) in water (70 ml). The insoluble material was filtered off and the filtrate was concentrated to dryness. The residue was dissolved in ethyl acetate (100 ml) and the solution was filtered. The filtrate was stirred at room temperature and the precipitates were filtered and washed with ethyl acetate to give colorless crystals of 4'-cyano-2'-(2,4-difluorophenoxy)methanesulfonanilide sodium salt (14.8 g).

mp: 267° to 268° C.

IR (Nujol): 2240, 1600, 1500, 1330, 1250, 1120 cm$^{-1}$.

NMR (CD$_3$OD, δ): 2.89 (3H, s), 6.8–7.6 (6H, m).

EXAMPLE 74

4'-Cyano-2'-(2,4-difluorophenoxy)methanesulfonanilide (50 g) was dissolved in ethyl acetate (1000 ml) at 50° C. and the insoluble was filtered off. To the filtrate was added 25% sodium hydroxide solution (27.2 g). The resulting solution was concentrated to about 500 ml under reduced pressure and stirred at 30° C. for 4 hours. The precipitates were filtered and washed with ethyl acetate (50 ml) to give colorless crystals of 4'-cyano-2'-(2,4-difluorophenoxy)methanesulfonanilide sodium salt (48.2 g).

This object compound was identical to the object compound of Example 73 by comparing both physical data.

EXAMPLE 75

4'-Cyano-2'-(2,4-difluorophenoxy)methanesulfonanilide (48.6 g) was dissolved in a solution of sodium hydroxide (12 g) in water (486 ml). The mixture was filtered and the filtrate was stirred at room temperature for 1 hour. The precipitates were filtered and washed with water (96 ml) to give colorless crystals of 4'-cyano-2'-(2,4-difluorophenoxy)methanesulfonanilide sodium salt (46 g).

This compound was identical to the object compound of Example 73 by comparing both physical data.

EXAMPLE 76

4'-Cyano-2'-(2,4-difluorophenoxy)methanesulfonanilide (10 g) was dissolved in 5% sodium hydroxide solution (100 ml). The solution was extracted with ethyl acetate (250 ml). The extract was concentrated to 100 ml and the resulting mixture was stirred at room temperature for 30 minutes. The precipitates were filtered and washed with ethyl acetate to give colorless crystals of 4'-cyano-2'-(2,4-difluorophenoxy)methanesulfonanilide sodium salt (6 g).

This object compound was identical to the object compound by comparing both physical data.

We claim:

1. Alkanesulfonanilide derivatives of the formula:

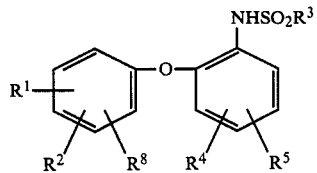

wherein

R¹, R² and R⁸ are each hydrogen, cyano, halogen, lower alkyl, halo(lower)alkyl, lower alkylthio, lower alkylsulfinyl, lower alkylsulfonyl or lower alkoxy, R³ is lower alkyl, R⁴ is acyl, cyano, carboxy, hydroxy(lower)alkyl, mercapto, lower alkylthio, lower alkylsulfinyl, lower alkylsulfonyl, 5-membered unsaturated heterocyclic group which may have amino, lower alkanoylamino, lower alkylthio or lower alkylsulfonyl, phenylthio which may have nitro or amino, lower alkanoyl(lower)alkenyl or a group of the formula:

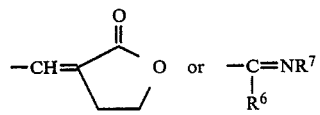

wherein

R⁶ is hydrogen, amino or lower alkyl and

R⁷ is hydroxy, lower alkoxy, carboxy(lower)alkoxy, lower alkoxycarbonyl(lower)alkoxy, ureido or thioureido, and R⁵ is hydrogen, halogen, lower alkyl or lower alkanoyl, and pharmaceutically acceptable salts thereof.

2. Alkanesulfonanilide derivatives according to claim 1, wherein R¹ and R² are each halogen, R⁸ is hydrogen, R³ is lower alkyl, R⁴ is acyl and R⁵ is hydrogen.

3. Alkanesulfonanilide derivatives according to claim 2, wherein R⁴ is lower alkanoyl.

4. Alkanesulfonanilide derivatives according to claim 1, wherein R¹ and R² are each fluorine, R⁸ is hydrogen, R³ is methyl, R⁴ is acetyl and R⁵ is hydrogen.

5. Alkanesulfonanilide derivatives according to claim 1, wherein R¹ and R² are each halogen, is hydrogen, R³ is lower alkyl, R⁴ is cyano and R⁵ is hydrogen.

6. Alkanesulfonanilide derivatives according to claim 1, wherein R¹ and R² are each fluorine, R⁸ is hydrogen, R³ is methyl, R⁴ is cyano and R⁵ is hydrogen 7. Alkanesulfonanilide derivative according to claim 1, which is 4'-acetyl-2'-(2,4-difluorophenoxy)methanesulfonanilide.

8. Alkanesulfonanilide derivative according to claim 1, which is 4'-cyano-2'-(2,4-difluorophenoxy)methanesulfonanilide.

9. A pharmaceutical composition comprising an effective amount of one or more alkanesulfonanilide derivatives as defined in claim 1 or pharmaceutically acceptable salt thereof in admixture with a carrier.

10. An antiinflammatory composition comprising an effective amount of one or more alkanesulfonanilide derivatives as defined in claim 1 or pharmaceutically acceptable salt thereof in admixture with a carrier.

11. An analgesic composition comprising an effective amount of one or more alkanesulfonanilide derivatives as defined in claim 1 or pharmaceutically acceptable salt thereof in admixture with a carrier.

12. An antipyretic composition comprising an effective amount of one or more alkanesulfonanilide derivatives as defined in claim 1 or pharmaceutically acceptable salt thereof in admixture with a carrier.

13. A method of treating inflammatory diseases which comprises administering to a subject in need of such treatment an effective amount of the composition of claim 10.

14. A method of treating pains which comprises administering to a subject in need of such treatment an effective amount of the composition of claim 11.

15. A method of treating pyretic diseases which comprises administering to a subject in need of such treatment an effective amount of the composition of claim 12.

16. A method of treating rheumatism which comprises administering to a subject in need of such treatment an effective amount of the composition of claim 10.

17. A method of treating arthritis which comprises administering to a subject in need of such treatment an effective amount of the composition of claim 10.

18. Alkanesulfonanilide derivative according to claim 1, which is 4'-cyano-2'-(2,4-difluorophenoxy)methanesulfonanilide sodium salt.

* * * * *

UNITED STATES PATENT AND TRADEMARK OFFICE
CERTIFICATE OF CORRECTION

PATENT NO. : 4,866,091

DATED : September 12, 1989

INVENTOR(S) : Masaaki Matsuo, et al.

It is certified that error appears in the above-identified patent and that said Letters Patent is hereby corrected as shown below:

On the title page, item [57]:
In the Abstract, "alkane-sulfonanilide should be
--Alkanesulfonanilide--.

Column 11, line 29, "earth metal salt e.g." should be
--earth metal salt (e.g.--.

Column 12, line 62, "thyleneaminocarbonyl," should be
--thyleneaminocarbonyl--.

Column 18, lines 58, 60, "(I')" should be --($I^i$)--;
line 68, "not have are adverse" should be
--not have an adverse--.

Column 21, line 18, "unijected" should be --uninjected--.

Column 22, line 37, "Sprague Dawley" should be
--Sprague-Dawley--;
line 39, "hind paw, The" should be --hind paw. The--;
line 66, "sweetning agents," should be
--sweetening agents,--.

Column 31, line 25, "3360 1655" should be --3360, 1655--.

Column 32, line 52, "4 Amino-3 (" should be --4-Amino-3-(--.

Column 33, line 26, "2.60 3H" should be --2.60 (3H--;
line 32, "trichlcrophenoxy" should be
--trichlorophenoxy--;
line 61, "2.25 3H" should be --2.25 (3H--.

UNITED STATES PATENT AND TRADEMARK OFFICE
CERTIFICATE OF CORRECTION

PATENT NO. : 4,866,091

DATED : September 12, 1989

INVENTOR(S) : Masaaki Matsuo, et al.

It is certified that error appears in the above-identified patent and that said Letters Patent is hereby corrected as shown below:

Column 34, line 3, "Preparation 71" should be
--PREPARATION 71-- (in capital letters, centered);
line 13, "at to" should be --at 0° to--.

Column 35, line 21, "for hours." should be --for 3 hours.--.

Column 36, line 14, "(Nujol) 1700" should be
--(Nujol):1700--;
line 15, "d6,6" should be --$d_6$,δ--;
line 23, "]dithiocarbamate" should be
--]-dithiocarbamate--.

Column 37, line 4, "y)acetophenone" should be
--y)-acetophenone--;
line 14, "CDC13 6" should be --$CDCl_3$,δ--.

Column 39, line 57, "(M+," should be --(M+),--.

Column 40, line 16, "(M+," should be --(M+),--.

Column 42, line 38, "an cil" should be --an oil--;
line 38, "(tertbutyloxycarbonylmethoxyimino)" should be --(tert-butyloxycarbonylmethoxy-imino)--.

Column 44, line 44, "δ);" should be --δ):--.

Column 46, line 33, "on acetate" should be --on silica fel (60g) eluting with a mixture of toluene and ethyl acetate--.

UNITED STATES PATENT AND TRADEMARK OFFICE
CERTIFICATE OF CORRECTION

PATENT NO. : 4,866,091

DATED : September 12, 1989

INVENTOR(S) : Masaaki Matsuo, et al.

Page 3 of 3

It is certified that error appears in the above-identified patent and that said Letters Patent is hereby corrected as shown below:

Column 47, line 27, "powder 0.76" should be --powder (0.76--;
          line 40, "3-'chloro" should be --3'-chloro--;
          line 67, should be --3.10(3H,s),6.8-7.4(5H,M),
              7.56(1H,s)--.

Column 48, line 63, should be --MASS(M/E): 361(M+),346--.

Column 50, line 3, "cilica" should be --silica--.

Column 51, between lines 52 and 53, insert --Example 70--

Column 52, line 6, "(Nujol) 3300" should be --(Nujol):3300--.

Signed and Sealed this

Fifth Day of February, 1991

Attest:

HARRY F. MANBECK, JR.

*Attesting Officer*

*Commissioner of Patents and Trademarks*